(12) United States Patent
Sarpeshkar et al.

(10) Patent No.: US 8,000,797 B1
(45) Date of Patent: Aug. 16, 2011

(54) SYSTEMS AND METHODS FOR PROVIDING NEURAL STIMULATION WITH AN ASYNCHRONOUS STOCHASTIC STRATEGY

(75) Inventors: Rahul Sarpeshkar, Arlington, MA (US); Michael A. Faltys, Northridge, CA (US); Ji-Jon Sit, Cambridge, MA (US)

(73) Assignees: Advanced Bionics, LLC, Valencia, CA (US); Massachusetts Institute of Technology, Cambridge, MA (US)

( * ) Notice: Subject to any disclaimer, the term of this patent is extended or adjusted under 35 U.S.C. 154(b) by 284 days.

(21) Appl. No.: 11/449,056

(22) Filed: Jun. 7, 2006

(51) Int. Cl.
*A61N 1/00* (2006.01)
*A61B 5/04* (2006.01)

(52) U.S. Cl. .............. 607/57; 607/5; 607/55; 600/372

(58) Field of Classification Search .............. 607/50, 607/55, 57; 600/372
See application file for complete search history.

(56) References Cited

U.S. PATENT DOCUMENTS

| | | | |
|---|---|---|---|
| 4,284,856 A * | 8/1981 | Hochmair et al. ............ 607/9 |
| 4,819,647 A | 4/1989 | Byers et al. |
| 5,597,380 A * | 1/1997 | McDermott et al. ......... 607/57 |
| 5,603,726 A | 2/1997 | Schulman et al. |
| 5,776,172 A * | 7/1998 | Schulman et al. ............ 607/56 |
| 5,876,443 A * | 3/1999 | Hochmair et al. ............ 623/10 |
| 5,999,859 A * | 12/1999 | Jolly ............................ 607/137 |
| 6,078,838 A | 6/2000 | Rubinstein |
| 6,091,994 A | 7/2000 | Loos |
| 6,129,753 A | 10/2000 | Kuzma |
| 6,132,384 A | 10/2000 | Christopherson et al. |
| 6,181,969 B1 | 1/2001 | Gord |
| 6,219,580 B1 * | 4/2001 | Faltys et al. ................. 607/57 |
| 6,242,988 B1 | 6/2001 | Sarpeshkar |
| 6,272,382 B1 * | 8/2001 | Faltys et al. ................. 607/57 |
| 6,289,247 B1 * | 9/2001 | Faltys et al. ................. 607/57 |
| 6,308,101 B1 | 10/2001 | Faltys et al. |
| 6,321,125 B1 * | 11/2001 | Kuzma ........................ 607/137 |
| 6,390,971 B1 * | 5/2002 | Adams et al. ................ 600/25 |
| 6,572,531 B2 * | 6/2003 | Zilberman et al. .......... 600/25 |
| 6,604,283 B1 * | 8/2003 | Kuzma ........................ 29/857 |
| 6,631,295 B2 | 10/2003 | Rubinstein et al. |
| 6,732,073 B1 * | 5/2004 | Kluender et al. ............ 704/233 |
| 6,751,505 B1 | 6/2004 | Van Den Honert |
| 6,778,858 B1 * | 8/2004 | Peeters ........................ 607/57 |
| 6,788,975 B1 | 9/2004 | Whitehurst et al. |
| 6,819,957 B1 | 11/2004 | Le |
| 6,845,271 B2 | 1/2005 | Fang et al. |
| 6,915,166 B1 * | 7/2005 | Stecker et al. ............... 607/55 |
| 7,292,892 B2 * | 11/2007 | Litvak et al. ................. 607/57 |
| 2005/0192646 A1 * | 9/2005 | Grayden et al. ............. 607/57 |

OTHER PUBLICATIONS

Cauwenberghs et al., "A charge-based CMOS parallel analog vector quantizer", Adv. Neural Inform. Proc. Syst (NIPS), Denver, CO. vol. 7, 1994.

(Continued)

*Primary Examiner* — Niketa I Patel
*Assistant Examiner* — Nicole F Lavert
(74) *Attorney, Agent, or Firm* — AdvantEdge Law Group, LLC

(57) ABSTRACT

The present invention provides methods and systems for selecting one or more channels of a neural implant to stimulate. A channel selection unit is configured to asynchronously and stochastically select the winning channel or channels based, in part, on the richness of the input sensory environment. Thereafter, the channel selection unit reduces the likelihood that the selected channel or channels will be selected again for a period of time.

48 Claims, 18 Drawing Sheets

OTHER PUBLICATIONS

Chen et al., "Frequency modulation detection in cochlear implant subjects," *The Journal of the Acoustical Society of America*, vol. 116, pp. 2269-2277, 2004.

Dayan et al., "Computational and Mathematical Modeling of Neural Systems", Theoretical Neuroscience, The MIT Press, pp. 162-165, 2001.

Dorman et al., "A comparison of the speech understanding provided by acoustic models of fixed-channel and channel-picking signal processors for Cochlear implants," *Journal of Speech, Language, and Hearing Research*, vol. 45, pp. 783-788, 2002.

Fu et al., "Effects of noise and spectral resolution on vowel and consonant recognition: Acoustic and electric hearing," *The Journal of the Acoustical Society of America*, vol. 104, pp. 3586-3596, 1998.

Gulya, "Transcription of Open Session, Ear, Nose and Throat Devices Panel," *Food and Drug Administration Center for Devices and Radiological Health*, 2002.

Hahnloser et al., "Digital Selection and Analogue Amplification Coexist in a Cortex-Inspired Silicon Circuit", Nature, vol. 405, pp. 947-951, 2000.

Kasturi, et al., "Effect of Filtering Spacing and Correct Tonotopic Representation on Melody Recognition: Implications for Cochlear Implants," *Proceedings of the Association for Research in Otolaryngology*, 2005.

Lan et al., "A novel speech-processing strategy incorporating tonal information for cochlear implants," *Biomedical Engineering, IEEE Transactions on*, vol. 51, pp. 752-760, 2004.

Lazzaro et al., "Winner-take-all networks of O(n) complexity", Advances in Neural Information Processing Systems (Touretzsky, D.S., ed.), vol. 2, Morgan Kaufmann, San Mateo, CA, pp. 703-711, 1989.

Litvak et al., Auditory nerve fiber responses to electric stimulation: Modulated and unmodulated Pulse trains. J. Acoust. Soc. Am, vol. 110, No. 1, pp. 368-379, 2001.

Litvak et al., "Desynchronization of electrically evoked auditory-nerve activity by high-frequency pulse trains of long duration," *The Journal of the Acoustical Society of America*, vol. 114, pp. 2066-2078, 2003.

Litvak et al., "Improved temporal coding of sinusoids in electric stimulation of the auditory nerve using desynchronizing pulse trains", J. Acoust. Soc. Am, vol. 114, No. 4, pt 1, pp. 2079-2098, 2003.

Litvak et al. "Improved neural representation of vowels in electric stimulation using desynchronizing pulse trains," *The Journal of the Acoustical Society of America*, vol. 114, pp. 2099-2111, 2003.

Loizou, "Mimicking the human ear," *Signal Processing Magazine, IEEE*, vol. 15, pp. 101-130, 1998.

Loizou, "Introduction to Cochlear Implants", IEEE Engineering in Medicine and Biology Magazine, vol. 18, No. 1, pp. 32-42, 1999.

Najafi et al., "A Modular 32-Site Wireless Neural Stimulation Microsystem", IEEE J. Solid State Circuits, vol. 39, No. 12, pp. 2457-2466, 2004.

Nie et al., "Encoding frequency Modulation to improve cochlear implant performance in noise," *Biomedical Engineering, IEEE Transactions on*, vol. 52, pp. 64-73, 2005.

Qin et al., "Role of F0 in speech reception in the presence of interference : simulating aspects of cochlear-implant processing," 2005, pp. 125 leaves.

Rubinstein et al., "Pseudospontaneous activity: stochastic independence of auditory nerve fibers with electrical stimulation", Hearing Research 127, pp. 108-118, 1999.

Sarpeshkar et al., "An ultra-low-power programmable analog bionic ear processor," *Biomedical Engineering, IEEE Transactions on*, vol. 52, pp. 711-727, 2005.

Sarpeshkar et al., "A Low-Power Wide-Dynamic-Range Analog VLSI Cochlea", Analog Integrated Circuits and Signal Processing, Kluwer Academic Publishers, vol. 16, pp. 245-274, 1998.

Sarpeshkar et al., "An Analog Bionic Ear Processor with Zero-Crossing Detection", Proceedings of the IEEE International Solid-State Circuits Conference, Feb. 2005.

Sarpeshkar et al., "Scalable Hybrid Computation with Spikes", Neural Computation, Massachusetts Institute of Technology, pp. 2003-2038, 2002.

Shannon et al., "Speech Recognition with Primarily Temporal Cues," *Science*, vol. 270, pp. 303-304, 1995.

Siebert, *Circuits, signals, and systems*. Cambridge, Mass.: MIT Press, chapter 17, pp. 527-530, 1986.

Smith et al.,"Chimaeric sounds reveal dichotomies in auditory perception", Nature, vol. 416, pp. 87-90, 2002.

Stein, "A Theoretical Analysis of Neuronal Variability", Biophys. J., vol. 5, pp. 173-194, 1965.

Stickney et al., "Contribution of frequency modulation to speech recognition in noise," *The Journal of the Acoustical Society of America*, vol. 118, pp. 2412-2420, 2005.

Wessel et al., "Coding of Time-Varying Electric Field Amplitude Modulations in a Wave-Type Electric Fish", J. Neurophys, vol. 75, No. 6, pp. 2280-2293, 1996.

Wilson et al., "Better speech recognition with cochlear implants," *Nature*, vol. 352, pp. 236-238, 1991.

Zeng, "Temporal pitch in electric hearing," *Hearing Res.*, vol. 174, pp. 101-106, 2002.

\* cited by examiner

STEP NO. PSEUDOCODE 52.1 ....... INITIALIZE CAPACITOR VOLTAGES: $V_{cap(t)}$ = 0 FOR ALL CHANNELS 52.2 ....... INITIALIZE TIME OF LAST SPIKE: $t_{lastspike}$ = -∞ FOR ALL CHANNELS 52.3 ....... INITIALIZE SPIKING OUTPUT: $spike(t)$ = 0 FOR ALL CHANNELS 52.4 ....... COMPUTE INHIBITION CURRENT: $I_{inh}(t) = A_{inh} * H_{inh}(t-t_{lastspike})$ FOR EACH CHANNEL AT EACH TIME INCREMENT 52.5 ....... INCREMENT CAPACITOR VOLTAGE: $V_{cap}(t)$ += $max[HWR(t) - I_{inh}(t), 0]$ FOR EACH CHANNEL AT EACH TIME INCREMENT 52.6 ....... IF ANY CHANNELS EXCEED THRESHOLD VOLTAGE: $max[V_{cap}(t)$ OF ALL CHANNELS] > $V_{thresh}$ 52.7 ............ FIND WINNING CHANNEL: $max\_ch$ = CHANNEL WITH $max[V_{cap}(t)$ OF ALL CHANNELS]

52.8 ............ REINITIALIZE CAPACITOR VOLTAGES: $V_{cap}(t)$ = 0 FOR ALL CHANNELS 52.9 ............ SET SPIKE OUTPUT FOR WINNING CHANNEL: $spike(t) = E(t)$ FOR WINNING CHANNEL $max\_ch$ 52.10 .......... SET $t_{lastspike} = t$ FOR WINNING CHANNEL $max\_ch$

FIG. 3B

SYSTEMS AND METHODS FOR PROVIDING NEURAL STIMULATION WITH AN ASYNCHRONOUS STOCHASTIC STRATEGY

FIELD OF THE INVENTION

The present invention relates to systems and methods for providing neural stimulation across multiple electrode channels using an asynchronous stochastic stimulation strategy.

BACKGROUND OF THE INVENTION

A human ear comprises an outer ear, a middle ear, and an inner ear. The outer ear picks up acoustic pressure waves, which are converted into mechanical vibrations in the middle ear. In the inner ear, a cochlea, which is a snail-shaped cavity filled with cochlear fluid, converts the mechanical vibrations into pressure waves, causing a basilar membrane to displace. This in turn displaces hair cells in contact with the basilar membrane, causing associated biological neurons to fire. These biological neurons communicate with the central nervous system via the auditory nerve to transmit information about the acoustic signal to the brain. The brain then registers the information as perceptions of sound.

Hearing loss, which may be due to many different causes, generally comprises two types: conductive and sensorineural. Conductive hearing loss occurs when the normal mechanical pathways for sound to reach the hair cells in the cochlea are impeded. Conductive hearing loss often may be helped by use of conventional hearing aids, which amplify sound so that acoustic information reaches the cochlea and the hair cells. Sensorineural hearing loss, on the other hand, is usually due to the absence or impairment of the hair cells which are needed to transduce acoustic signals in the cochlea into nerve impulses that are sent to the auditory nerve. People suffering from sensorineural hearing loss are usually unable to derive any benefit from conventional hearing aid systems because their mechanisms for transducing sound energy into auditory nerve impulses are non-existent or have been severely damaged.

Cochlear implant technology seeks to overcome sensorineural hearing loss by bypassing the hair cells in the cochlea and presenting electrical stimulation to the biological neurons directly, leading to the perception of sound in the brain and at least partial restoration of hearing. Cochlear implant technology may be used to bypass the outer, middle and inner ears. Cochlear implant systems that utilize such technology have been successfully used to restore hearing in sensorineurally deaf patients.

Generally, a cochlear implant system includes a power source, a microphone, a signal processing device, a stimulation device and an electrode array, one or more of which may be implanted within the patient. The power source supplies power to the system. Sound enters the system through the microphone which delivers it to the signal processing device as an electrical signal. The signal processing device processes the signal and stimulates electrodes in an electrode array that is implanted in the cochlea based on the processed signals. The electrodes in the array transmit electrical stimuli to the nerve cells or biological neurons associated with the cochlea. These nerve cells are arranged in an orderly tonotopic sequence, from high frequencies near the initial (basal) end of the cochlear coil to progressively lower frequencies towards the inner end of the coil (apex). Nerve cells emanating from the various regions of the cochlea are associated with the frequencies that most efficiently stimulate those regions. The brain, which receives neural impulses from the auditory nerve, maps those frequencies in accord with this association.

Conventional cochlear implants separate sound signals into a number of parallel channels of information, each representing the intensity of a narrow band of frequencies within the acoustic spectrum. Ideally, each channel of information would be conveyed selectively to the subset of nerve cells located along the cochlea that would have normally transmitted information about that frequency band to the brain. The electrode array is typically inserted into the scala tympani, one of the three parallel ducts that make up the spiral shape of the cochlea. The array of linearly arranged electrodes is inserted such that the electrode closest to the basal end of the coil is associated with the highest frequency band and the electrode closest to the apex is associated with the lowest frequency band. Each location along the implanted length of the cochlea may be mapped to a corresponding frequency, thereby yielding a frequency-to-location table for the electrode array. The foregoing illustrates the relationship between frequency and physical location in the cochlea—i.e., the cochlear frequency/location correspondence.

Many pulsatile neural stimulators, particularly in the case of cochlear implant stimulators, employ a fixed-rate stimulation strategy, in which amplitude-modulated current pulses are generated for each channel at a fixed frequency and used to stimulate the implanted electrodes. However, studies have shown that fixed-rate stimulation may differ from biological acoustic stimulation for many reasons. First, biological acoustic stimulation of the cochlea produces much less across-fiber synchrony and much more within-fiber jitter than electrical stimulation from a cochlear implant that employs a fixed rate stimulation strategy. Second, in fixed-rate stimulation, low rate stimulation (less than approximately 800 Hz) causes entrainment of the response—that is, a deterministic neural discharge once per stimulus cycle at the fixed rate of the carrier—and temporally-precise phase-locking to the carrier (i.e., a fixed-rate pulse train), even though the carrier contains no useful information about the sound environment. Those effects do not occur in biological acoustic stimulation. Third, in fixed-rate stimulation, high rate stimulation (greater than approximately 800 Hz) causes neural spiking to occur at highly regular intervals determined by the relative refractory period (that is, the time for a neuron to recover from a previous discharge) and may cause sever distortions in the temporal discharge patterns as a result of neural refractoriness. Studies have shown that the distributions of interspike interval (ISI) and modal period (MP) histograms of fixed rate stimulation systems are concentrated at the refractory period and phase (respectively). Such regular neural spiking and phase are unnatural compared to biological acoustic stimulation, which tend to have ISI and MP histograms that exhibit wider distributions. These effects that are observed in fixed rate stimulation systems stem from neuronal synchronization to the fixed rate of the stimulation carrier and interaction between electrodes.

In view of the foregoing, it would be desirable to be able to provide systems and methods for providing neural stimulation with an asynchronous character. As used herein, the term "asynchronous stimulation" means that the rate or rates at which nerve cells are stimulated are not limited to fixed rate or rates. Thus, the stimulation rate or rates may be adjusted dynamically.

It also would be desirable to be able to provide systems and methods for providing neural stimulation in which each channel is stimulated in a stochastic manner.

It further would be desirable to be able to provide systems and methods for conveying phase information during neural stimulation.

It even further would be desirable to be able to provide systems and methods for providing neural stimulation with reduced power.

It additionally would be desirable to be able to provide systems and methods for providing neural stimulation that more closely resembles biological acoustic stimulation.

SUMMARY OF THE INVENTION

In view of the foregoing, it is an object of the present invention to provide systems and methods for providing neural stimulation with an asynchronous character.

It also is an object of the present invention to provide systems and methods for providing neural stimulation in which each channel is stimulated in a stochastic manner.

It further is an object of the present invention to provide systems and methods for conveying phase information during neural stimulation.

It even further is an object of the present invention to provide systems and methods for providing neural stimulation with reduced power.

It additionally is an object of the present invention to provide systems and methods for providing neural stimulation that more closely resembles biological acoustic stimulation.

These and other objects of the present invention are accomplished by a neural stimulation device that employs an asynchronous, stochastic stimulation strategy. In a preferred embodiment of the present invention, a cochlear implant system having a sound processing unit coupled to an electrode array may be provided. The sound processing unit comprises, in part, a neural stimulation processing unit that incorporates a novel channel selection unit. The channel selection unit preferably is configured to select the channel or channels to be stimulated in the next successive stimulation cycle based on preprocessed signals that are representative of the sound environment. The channel selection unit then outputs a baseline or datum signal for those channels that were not selected and preferably a spike signal for the selected channel or channels. The spike signal or signals then are coupled to the preprocessed signals that are representative of the sound environment and then transmitted as stimulation signals to the appropriate electrodes after additional optional processing.

The channel selection unit of the present invention preferably employs the following steps. First, the channel selection unit accepts preprocessed signals as input signals from each channel of a preprocessor, the preprocessed signals representative of the sound environment. Second, the selection unit adjusts the preprocessed signals of one or more channels by one or more inhibition signals (if any) to generate effective input signals. For those channels for which there are no inhibition signals, their associated effective input signals equal their preprocessed signals. Third, the selection unit determines which channel or channels have the largest effective input signal(s). Fourth, the selection unit generates an output signal (e.g., a spike signal) for each of the winning channels. Fifth, the processing unit determines whether to generate an inhibition signal for the winning channel or each of the winning channels in accordance with an inhibition scheme. The inhibition signals are used to reduce or "weaken" the strength of the preprocessed signals corresponding to the winning channels to reduce the likelihood that the winning channel(s) will win again for a period of time. Preferably, the inhibition signals have initial maximum magnitudes that decay over time. To determine the next successive channel or channels to stimulate, the channel selection unit restarts from the first step.

BRIEF DESCRIPTION OF THE DRAWINGS

The above and other aspects, features and advantages of the present invention will be apparent upon consideration of the following detailed description, taken in conjunction with the accompanying drawings, in which like reference characters refer to like parts throughout, and in which:

FIG. 3B provides illustrative pseudo-code of race-to-spike algorithm of step 52 of the simulation illustratively presented with respect to FIG. 3A;

DETAILED DESCRIPTION OF THE INVENTION

The following description illustrates the neural stimulator of the present invention in the context of cochlear implants. It should be understood, however, that the neural stimulator of the present invention may be employed in a wide variety of other neural implants, such as retinal implants, deep-brain implants, and other implants that electrically stimulate biological neurons to translate a sensory environment that is external to a human being or animal. Considering the case of retinal implants, for example, the nerves that are stimulated would have a retinotopic arrangement as opposed to a tonotopic arrangement in the auditory nerve fibers that are stimulated by cochlear implants. Retinal implants would likewise benefit from many of the advantages that the present invention confers, e.g., mitigation of electrode interaction, delivery of phase information, and lower rates of stimulation. The neural stimulator of the present invention also may be employed in laryngeal implants, spinal cord implants, and other neural implants that electrically stimulate biological neurons to translate a sensory environment that is internal to a human being or animal. An example of such an internal sensory environment include actuation commands.

Figure 1A:
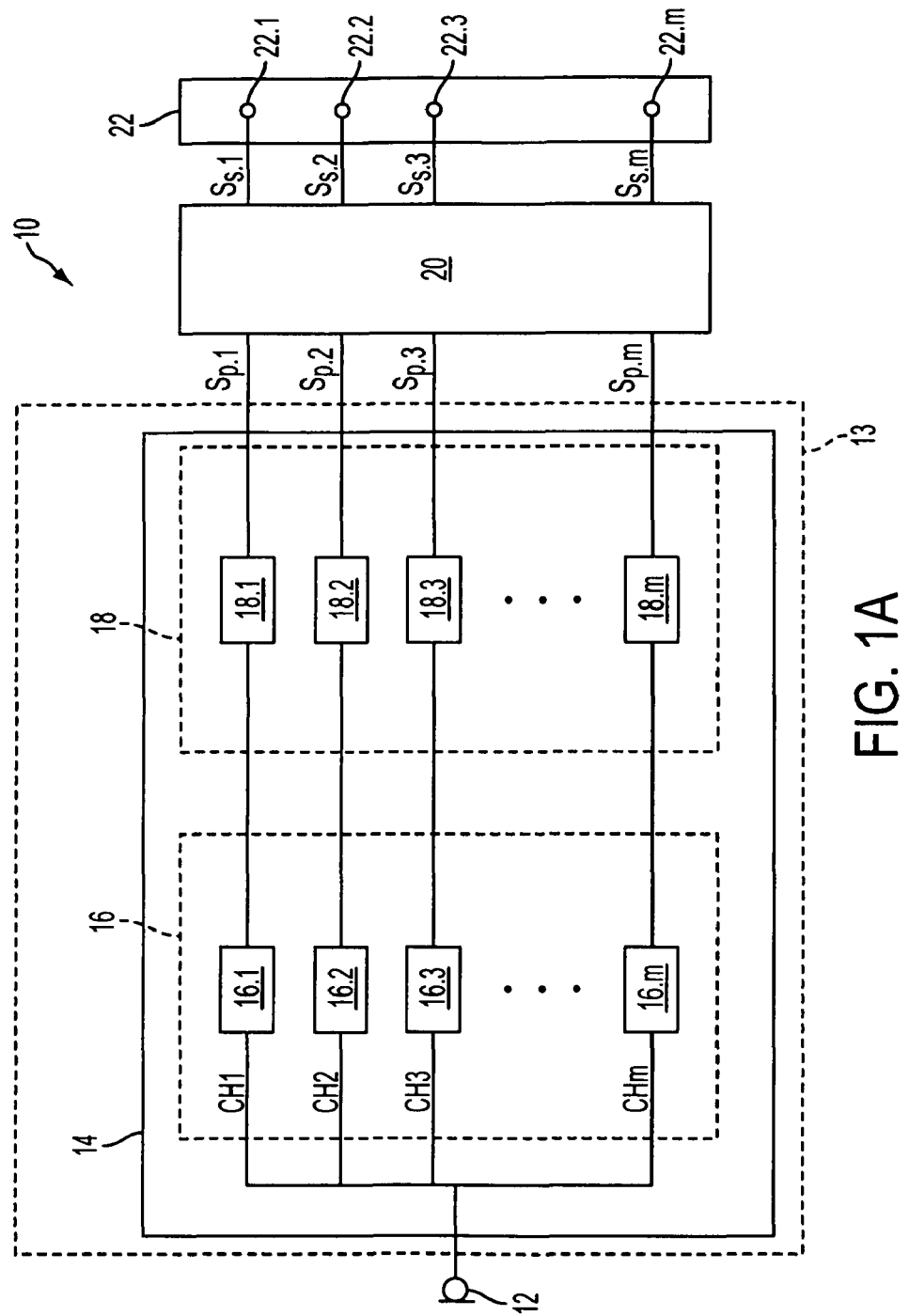
FIGS. 1A-1B are block diagrams of an illustrative cochlear implant of the present invention.
Figure 1B:
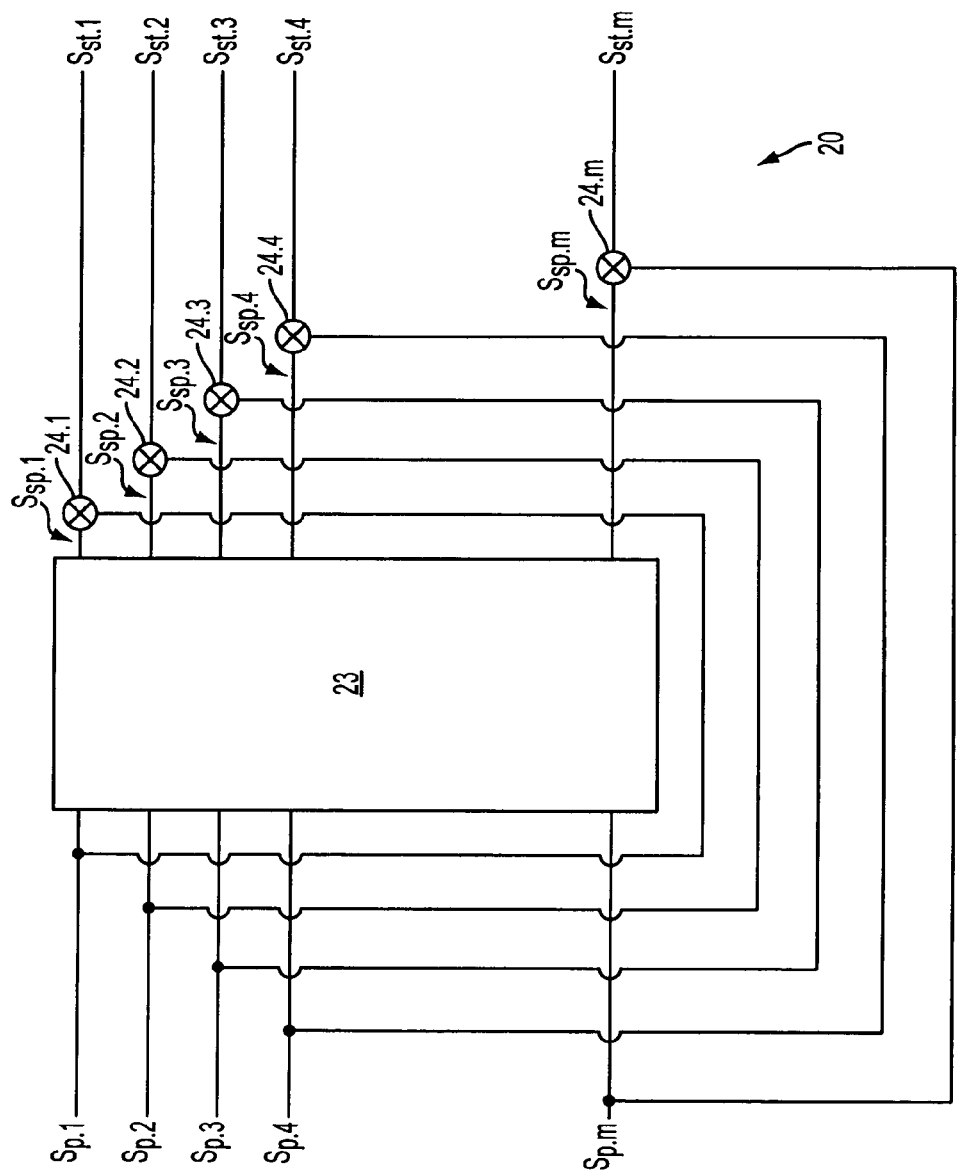

FIGS. 1A-1B are block diagrams of illustrative cochlear implant 10. Sound enters cochlear implant 10 through microphone 12, which transmits electrical signals representative of the sound waves to signal processing unit 13. Signal processing unit 13 comprises preprocessing unit 14 and neural stimulation processing unit 20. Preprocessing unit 14 may comprise modulated filter bank 16, which separates the sound signals from microphone 12 into a number of parallel channels of information (CH1, CH2 CH3 . . . CHm), each representing the intensity of a narrow band of frequencies within the acoustic spectrum. Each frequency channel may comprise one or more filters $16.x$, where x designates a channel number ranging from 1 to m. Each filter $16.x$ may incorporate one or more low-pass filters, band-pass filters, cochlear cascades, or combinations thereof. Cochlear cascades may be modeled after those described in "A Low-Power Wide-Dynamic-Range Analog VLSI Cochlea" by Sarpeshkar et al. (Analog Integrated Circuits and Signal Processing, Kluwer Academic Publishers, Vol. 16, pp. 245-274, 1998) or another type of cochlear cascade. Filter bank 16 also may comprise other filters known to one of ordinary skill in the art or otherwise.

Processing unit 14 also may comprise envelope detectors 18 to further process the outputs from filter bank 16 and extract or estimate the signal energy. Envelope detectors 18 may comprise half-wave or full-wave rectifiers, envelope detectors with different attack and release time constants, or other envelope detectors known to one of ordinary skill in the art or otherwise.

In addition, preprocessor 14 may include other preprocessing circuits, e.g., automatic gain control circuits to equalize loudness, signal compression circuits, and/or signal expansion circuits. For example, automatic gain control may be implemented before signals from the microphone are transmitted to filter bank 16. Non-linear compression circuits also may be employed to compress the dynamic range of the envelope output for each channel to fit into the dynamic range of its corresponding electrode.

After the sound signals are pre-processed by preprocessor 14, pre-processed signals $S_P.x$ (wherein x represents a channel number ranging from 1 to m) are delivered to neural stimulation processing unit 20 of the present invention, which accepts pre-processed signals $S_P.x$ from each channel of preprocessor 14. Signals $S_P.x$ contain time-varying amplitude and phase information. Using pre-processed signals $S_P.x$, the neural stimulation processing unit generates and transmits electrical stimulation signals $S_S.x$ to electrode array 22, instructing the electrodes to stimulate the nerve cells in a selective pattern. Processing unit 20 also encodes amplitude and phase information into stimulation signals $S_S.x$, as described in greater detail hereinbelow. Electrode array 22, which comprises at least one electrode $22.x$ for each channel, then stimulates the biological neurons directly in accordance with stimulation signals $S_S.x$. More thorough descriptions of certain aspects of cochlear implant 10 may be found, for example, in U.S. Pat. Nos. 4,819,647, 5,603,726, 5,776,172, 6,129,753, 6,181,969, 6,219,580, 6,289,247, 6,308,101, which are incorporated by reference herein in their entireties.

FIG. 1B provides a block diagram of neural stimulation processing unit 20. Processing unit 20 comprises channel selection unit 23 configured to select the channel or channels to be stimulated in succeeding stimulation cycles. As described in greater detail hereinbelow, channel selection unit 23 automatically selects the channel or channels according to the amplitudes of preprocessed signals $S_P.x$. Channel selection unit 23 then outputs a baseline or datum for signals $S_{SP}.x$ corresponding to those channels that were not selected (e.g., zero amplitude) and preferably a spike amplitude for signals $S_{SP}.x$ corresponding to the selected channel or channels. Combination circuits $24.x$ then couple signal $S_{SP}.x$ of each channel to the associated preprocessed signal $S_P.x$ for that channel, producing the resulting stimulation signals $S_{ST}.x$. Electrodes $22.x$ may be stimulated directly with stimulation signals $S_{ST}.x$ or may be stimulated with signals generated from further processing of stimulation signals $S_{ST}.x$, e.g., to fit the dynamic range of the associated electrode or the comfort level of a patient.

Combination circuits 24 may be configured to weight the spike strength as a function of signal $S_P.x$, which in the embodiment of FIG. 1A, represents the sound intensities of the corresponding channels (or the envelope magnitudes of the channels). In one embodiment, combination circuits 24 may be configured to weight output strengths by average past envelope magnitudes stored dynamically on capacitors associated with the respective channels. Such signals further may be scaled between an implant patient's threshold level of perception for a channel and the maximum level of perception for the same channel.

Figure 1C:
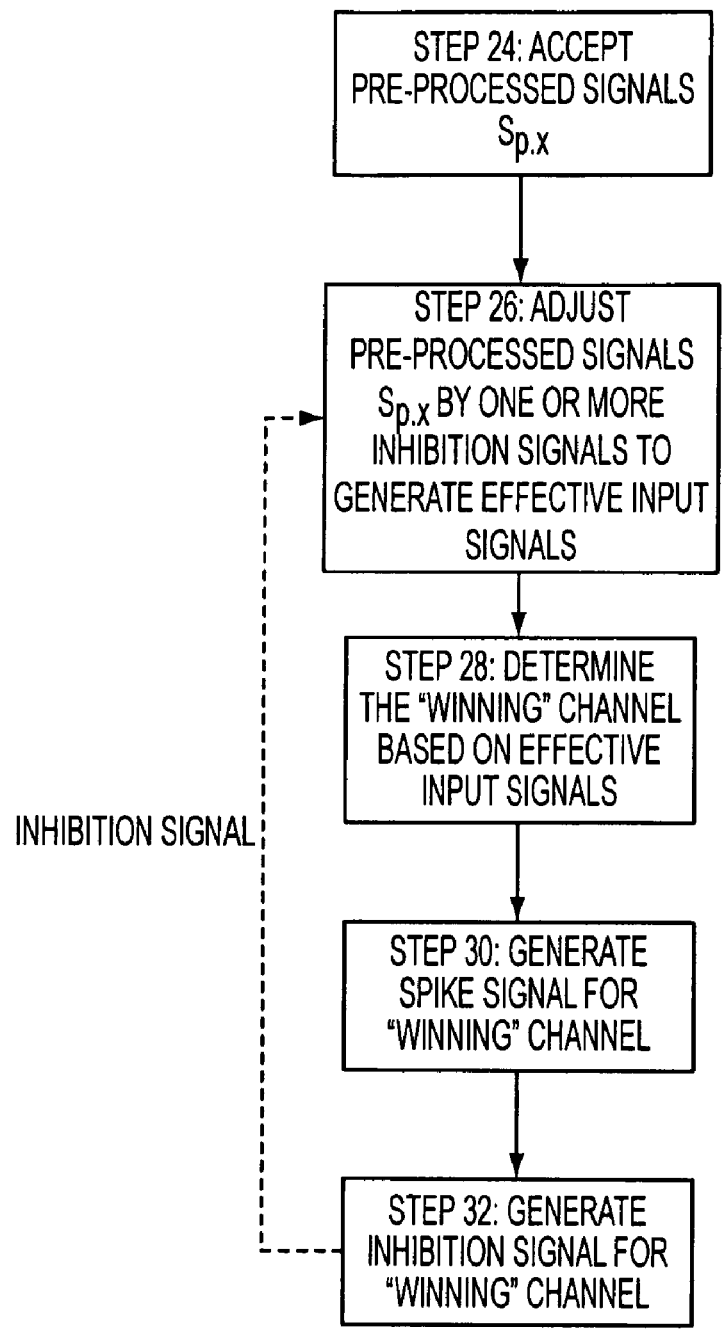
FIG. 1C is a flowchart of a channel selection strategy of the present invention for selecting an appropriate channel or channels to stimulate in a successive stimulation cycle.

In one embodiment, channel selection unit 23 of the present invention employs the algorithm illustrated in FIG. 1C in selecting an appropriate channel to stimulate in successive stimulation cycles. Advantageously, the strategy described with respect to FIG. 1C selects stronger channels to fire more often but also selects weaker channels to fire in proportion to their signal strength as well.

First, at step 24, channel selection unit 23 accepts preprocessed signals $S_P.x$ from each channel of preprocessor 14 as input signals. At step 26, the selection unit adjusts one or more preprocessed signals $S_P.x$ of one or more channels by one or more inhibition signals (if any) to generate an effective input signal for each channel. For a channel without an associated inhibition signal, its effective input signal will equal its pre-processed signal $S_P.x$. Thus, the effective input signal of a channel may be equal in magnitude to its corresponding input signal $S_P.x$. At step 28, the selection unit determines which channel has the largest effective input signal. That channel is the winning channel. The selection unit also may be configured to determine multiple winning channels, e.g., by determining a second winning channel that has the second largest effective input signal. At step 30, the selection unit generates an output signal $S_{SP}.x$ for each of the winning channels. Preferably, the output signal is a spike signal having a level that may be fixed over time and among all channels, fixed over time but varied over channels, or an arbitrarily complex function of its input. For example, the output level for a channel may be dependent on an average past envelope stored dynamically on a capacitor in that channel. At step 32, the processing unit determines whether to generate an inhibition signal for the winning channel in accordance with an inhibition scheme as discussed in greater detail hereinbelow. The inhibition signal is used to reduce or "weaken" the strength of preprocessed signal $S_P.x$ of the currently winning channel as discussed above in step 26. Superposition of the inhibition signal and preprocessed signal $S_P.x$ generates an effective input signal having lower magnitude or strength. A reduction in the magnitude of the effective input signal of a channel reduces the likelihood that the same channel will be selected as the winning channel in the next stimulation cycle. Depending on the inhibition scheme implemented, the inhibition signal will continue to reduce the magnitude of the effective input signal of the winning channel for a period of time. The algorithm then restarts from step 24.

To reduce the likelihood that a winning channel will win continuously, the present invention employs an inhibition scheme that defines parameters by which inhibition signals are generated for winning channels. Illustrative parameters include but are not limited to one or more of the following: the maximum level of an inhibition signal, the duration or time period during which an inhibition signal is generated, a decay or relaxation time constant or profile for an inhibition signal, and any other parameter useful to define the profile of an inhibition signal.

For example, the inhibition scheme may require that the inhibition signal have a maximum level and/or duration that is fixed, be proportional to how many times the associated electronic neuron (hereinafter "e-neuron") has won, be determined by some other arbitrarily complex function of the past behavior of the winning e-neuron, or be determined by an arbitrarily complex function that depends on the activity of other e-neurons, preprocessed signal $S_P.x$, time, an inhibition relaxation time constant, and/or any other parameter.

Additional examples include but are not limited to the following: (1) An inhibition signal, having a constant maximum for all channels, is generated for a channel each time the channel wins. (2) If a subset of channels is found to win all the time, then the inhibition signals are configured to ensure that the subset of channels will alternate in firing to inhibit or reduce the likelihood of successive firing in any one channel. (3) The relaxation of the inhibition signal is linear (i.e., has a fixed time constant of decay). (4) The relaxation of the inhibition signal is non-linear, e.g., the inhibition time constant being a function of the input amplitude in a channel. (5) The inhibition signal is scaled as a function of the number of times a channel has won in the past. For example, the inhibition signal is doubled if a channel wins twice in succession and quadrupled if it wins three times in succession. (6) A channel has to win a predetermined number of times before an inhibition signal is generated to weaken its associated input signal. Thus, the present invention only selectively generates inhibition signals for the winning channels depending on the inhibition scheme implemented; an inhibition signal may not actually be generated for a winning channel each time that channel wins. In a preferred embodiment, the inhibition signal has an initial maximum magnitude that decays over a predetermined period of time, thereby reducing the likelihood that the winning channel will win again for a predetermined period of time.

The "weakening" of a channel's input signal may last for a period determined by an inhibition relaxation time constant that may be fixed, an arbitrarily complex function of the past behavior of the winning e-neuron, or an arbitrarily complex function that depends on the activity of other e-neurons, preprocessed signal $S_P.x$, time, and/or any other appropriate parameters. The inhibition time constants also can be tailored to match neuronal time constants, thereby achieving mean firing rates that biologically are realistic, e.g., on the order of 150 Hz in spontaneously firing auditory nerve fibers. Advantageously, this may cause the inhibition signal to inhibit or reduce the likelihood that strong channels (that is, channels having more energy than other channels) will win deterministically, much like the refractory nature of a nerve. Alternatively, the present invention may comprise multi-rate time constants that scale with the center frequency of each channel. Each e-neuron may have customized or identical maximum inhibition levels and/or inhibition relaxation time constants.

One of ordinary skill in the art will recognize that, although the present description has illustrated the strategy of the present invention as being a linear sequence of events, the present invention is not so limited. For example, although step 32 has been presented as occurring after the output signal is generated for the winning channel in step 30, the inhibition signal can be generated simultaneously with the output signal. Furthermore, none of the steps described herein cease merely because another step is being carried out. For example, acceptance of input signals, generation of inhibition signals, and generation of effective input signals are continuously occurring processes that may be performed simultaneously.

Figure 2:
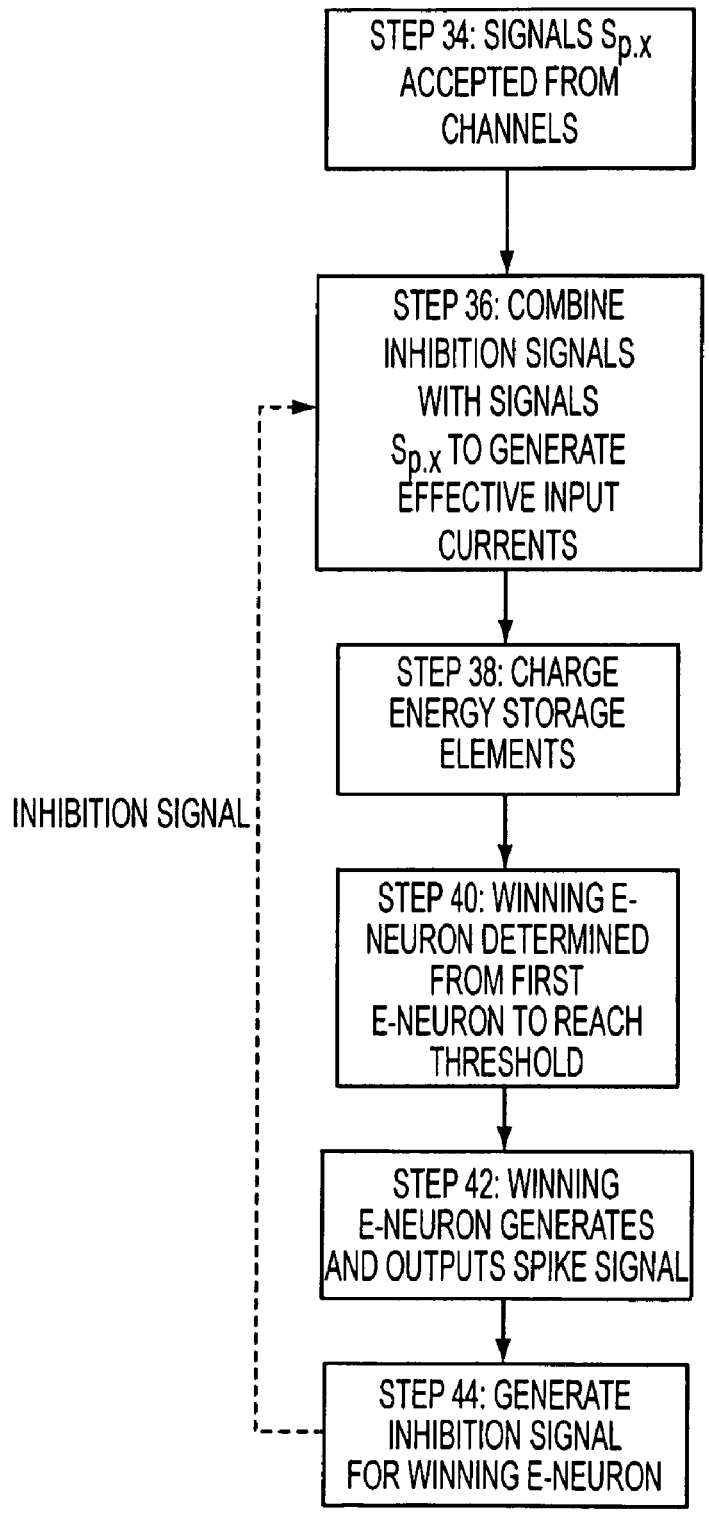
FIG. 2 is a flowchart of a first illustrative embodiment that employs the channel selection strategy of the present invention.

Referring to FIG. 2, a flowchart of a first illustrative embodiment of the present invention that employs the channel selection strategy discussed above is provided. The race-to-spike embodiment described with respect to FIG. 2 is based on N integrate-and-fire electronic neurons. See, e.g., U.S. Pat. No. 6,242,988 to Sarpeshkar, "Computational and Mathematical Modeling of Neural Systems" by Dayan et al. (Theoretical Neuroscience, The MIT Press, pp. 162-165, 2001), "Digital selection and analogue amplification coexist in a cortex-inspired silicon circuit" by Hahnloser et al. (Nature, Vol. 405, pp. 947-951, 2000), and "Scalable Hybrid Computation with Spikes" by Sarpeshkar et al. (Neural Computation, Massachusetts Institute of Technology, pp. 2003-2038, 2002), all of which are incorporated by reference herein in their entireties. Each channel of FIGS. 1A-1B comprises at least one electronic neuron.

In the race-to-spike embodiment, pre-processed signals $S_P.x$ from each channel of preprocessor 14 are accepted at step 34. At step 36, inhibition signals generated at step 44 are combined with preprocessed signals $S_P.x$ so that one or more of the preprocessed signals are weakened. The resulting effective input signals generate proportional charging signals, e.g., charging currents, to charge one or more energy storage elements, e.g., capacitors, associated with each channel at step 38. The start time at which the individual capacitors of the N e-neurons begin to charge is asynchronous and, as described in further detail below, arises automatically.

At step 40, the first e-neuron to have a voltage across the capacitor that equals or exceeds a predetermined threshold $V_{TH}'$ "wins." Threshold $V_{TH}'$ may be fixed over all stimulation cycles or may vary over time, such as one or more stimulation cycles. $V_{TH}'$ may also be fixed over all channels or vary over one or more channels, e.g., to create pre-emphasis or to accommodate different sensitivity to stimulation. $V_{TH}'$ also may vary over any other parameter in a predetermined or non-predetermined manner. Once a winning channel is determined, the voltages across the capacitors of the e-neurons are reset to zero or some datum level. This ensures that only one electrode can fire at any one time so that there are no overlapping stimulation periods. Advantageously, this avoids undesired electrode-interaction effects. At step 42, the winning e-neuron generates and outputs a spike output signal to be combined with its associated preprocessed signal $S_P.x$ by associated combination circuit 24.x.

At step 44, in accordance with an inhibition scheme, it is determined whether to generate an inhibition signal for the winning e-neuron to weaken its associated preprocessed signal $S_P.x$ at step 36. If appropriate, an inhibition signal is generated for the winning channel.

After an output signal is generated for the winning e-neuron, the neuronal race begins again at step 34, thereby establishing the start time at which the individual capacitors of the N e-neurons begin to charge.

The algorithm of FIG. 2 may be implemented by a software processor in conjunction with one or more power sources, e.g., current sources, configured to provide a stimulation signal to the electrodes in accordance with the cochlear implant system of the present invention. The algorithm of FIG. 2 also may be implemented using analog or digital circuits. See, e.g., U.S. Pat. No. 6,242,988 to Sarpeshkar, "Computational and Mathematical Modeling of Neural Systems" by Dayan et al. (Theoretical Neuroscience, The MIT Press, pp. 162-165, 2001), "Digital selection and analogue amplification coexist in a cortex-inspired silicon circuit" by Hahnloser et al. (Nature, Vol. 405, pp. 947-951, 2000), and "Scalable Hybrid Computation with Spikes" by Sarpeshkar et al. (Neural Computation, Massachusetts Institute of Technology, pp. 2003-2038, 2002).

Figure 3A:
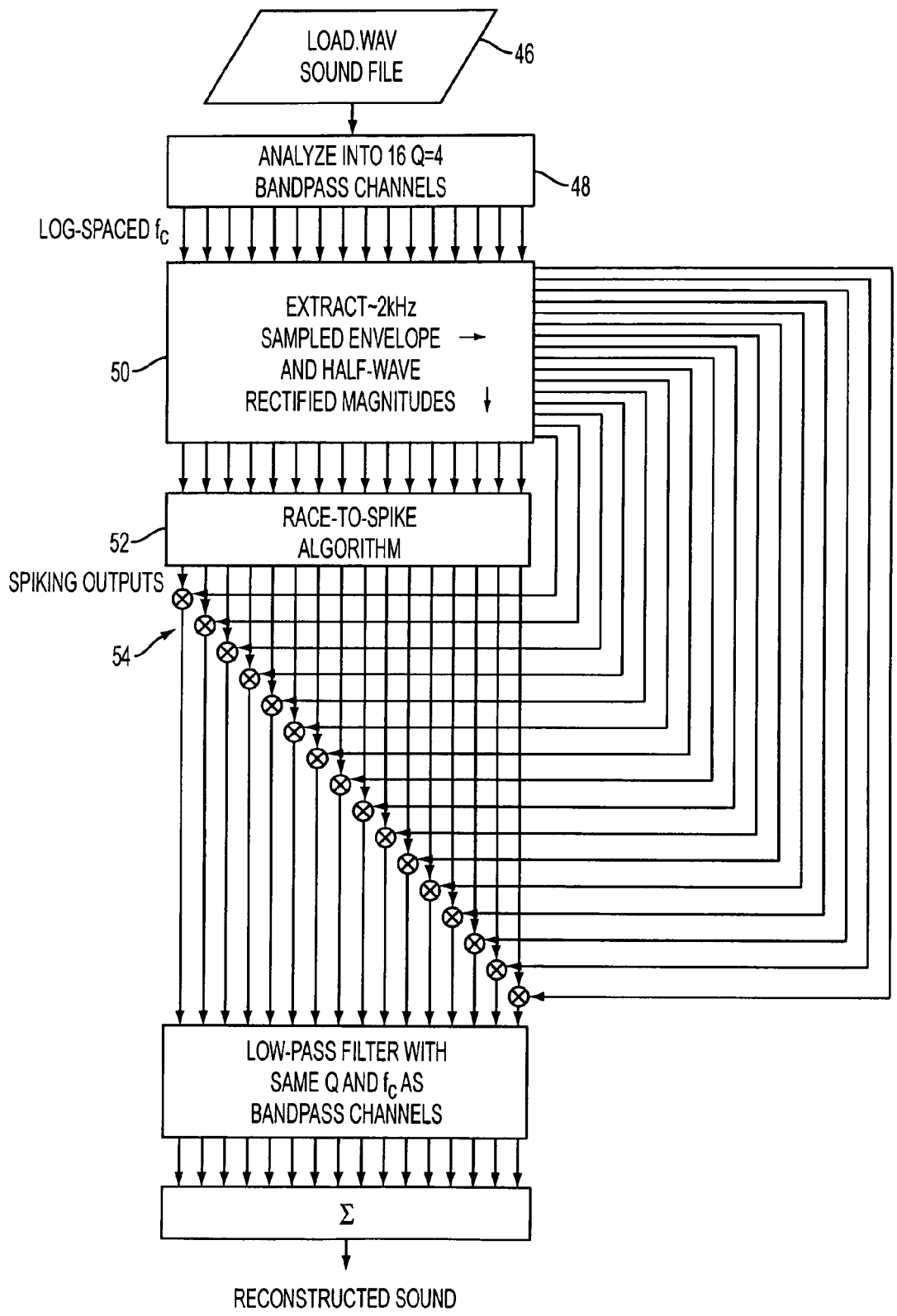
FIG. 3A is a flowchart of a simulation that applicants developed to simulate the embodiment of FIG. 2.

FIG. 3A provides a flowchart of a MATLAB simulation developed to simulate the race-to-spike algorithm of FIG. 2. First, at step 46, the simulation loads a sound file. Second, at step 48, the sound file is decomposed by a bank of 16 Q=4 band-pass filters at logarithmically spaced center frequencies from 116 Hz to 5024 Hz, where Q is the quality factor of the band-pass filters. Third, at step 50, the filter outputs (i.e., the envelope magnitude of each channel) are half-wave rectified for use as inputs to the race-to-spike algorithm. Fourth, at step 52, the above-described race-to-spike strategy is employed to determine successive winning e-neurons, generate and output successive output signals in the corresponding channels, and generate inhibition signals for the winning channels. Fifth, at step 54, the outputs from the race-to-spike algorithm are scaled by the filter outputs from step 50. The resulting signals represent stimulation signals that may be used to stimulate nerve cells.

The simulation modeled the reduction in inhibition current ($H_{inh}$) as a Fermi-Dirac function:

$$H_{inh}(t) = \frac{1}{1 + e^{k(t-\tau_{inh})}}$$

where k is a scaling factor that controls the steepness of the roll-off. When $t=\tau^{inh}$, $H_{inh}$ falls to half its initial value. This reduces the likelihood of firing for a minimum amount of time that is determined by the absolute refractory period to avoid wasting power by firing when almost all fibers are unable to respond. After that time, the Fermi-Dirac model permits the inhibition current to slowly decrease to permit a very strong input to overcome the inhibition. The Fermi-Dirac model also matches closely with the decrease in current output of a sub-threshold current source if the gate voltage on a pass transistor is linearly decreased. A single fixed maximum inhibition signal was used for all channels. A single fixed winning threshold $V_{TH}'$ was used for all channels. For simplicity, the spike signal strength was set to be uniform but could be weighted as a function of sound intensity, as discussed above.

FIG. 3B provides illustrative pseudocode to implement the race to spike algorithm (illustratively presented as step 52 of the flowchart of FIG. 3A). At step 52.1, variables $V_{cap}(t)$ storing the voltages across energy storage capacitors for all channels are initialized to zero. As described above with respect to steps 38 and 40 of FIG. 2, the first channel to have an input signal strength that charges its associated energy storage capacitor to a threshold voltage wins. At step 52.2, variables $t_{lastspike}$ storing the times at which each channel last won a race are initialized, e.g., to negative infinity, for all channels. At step 52.3, variables spike(t) storing the output signal strengths for all channels are initialized to zero.

At step 52.4, inhibition currents $I_{inh}(t)$ are computed for all channels as a function of $A_{inh}$ and $H_{inh}$, where $A_{inh}$ is the maximum magnitude of the inhibition current and $H_{inh}$ defines the reduction in the inhibition signal over time. $H_{inh}$ is a function of time t and time $t_{lastspike}$ at which the associated channel last won a race. At step 52.5, capacitor voltage $V_{cap}(t)$ of each channel is incremented by the input signal for the channel after any associated inhibition signal is subtracted therefrom. If the inhibition signal is greater in magnitude than the input signal, then voltage $V_{cap}(t)$ is incremented by zero.

At step 52.6, the program pseudocode determines whether any channels exceed threshold voltage $V_{thresh}$ by comparing the maximum value of capacitor voltages $V_{cap}$ for all the channels with threshold voltage $V_{thresh}$. If the capacitor voltage of at least one channel exceeds the threshold voltage, then the pseudocode determines which channel wins at step 52.7 Specifically, winning channel max_ch is the channel having the maximum capacitor voltage. Once the winning channel is determined, all voltages across the energy storing capacitors are reinitialized to zero at step 52.8 to prevent additional channels from firing. At steps 52.9 and 52.10, the magnitude of the output signal spike(t) and time $t_{lastspike}$ are set for the winning channel. Thereafter, the pseudocode loops back to step 52.4 to select the next winning channel. While the present invention was simulated using the illustrative pseudocode provided in FIG. 3B, the present invention is not limited thereto.

Figure 4A:
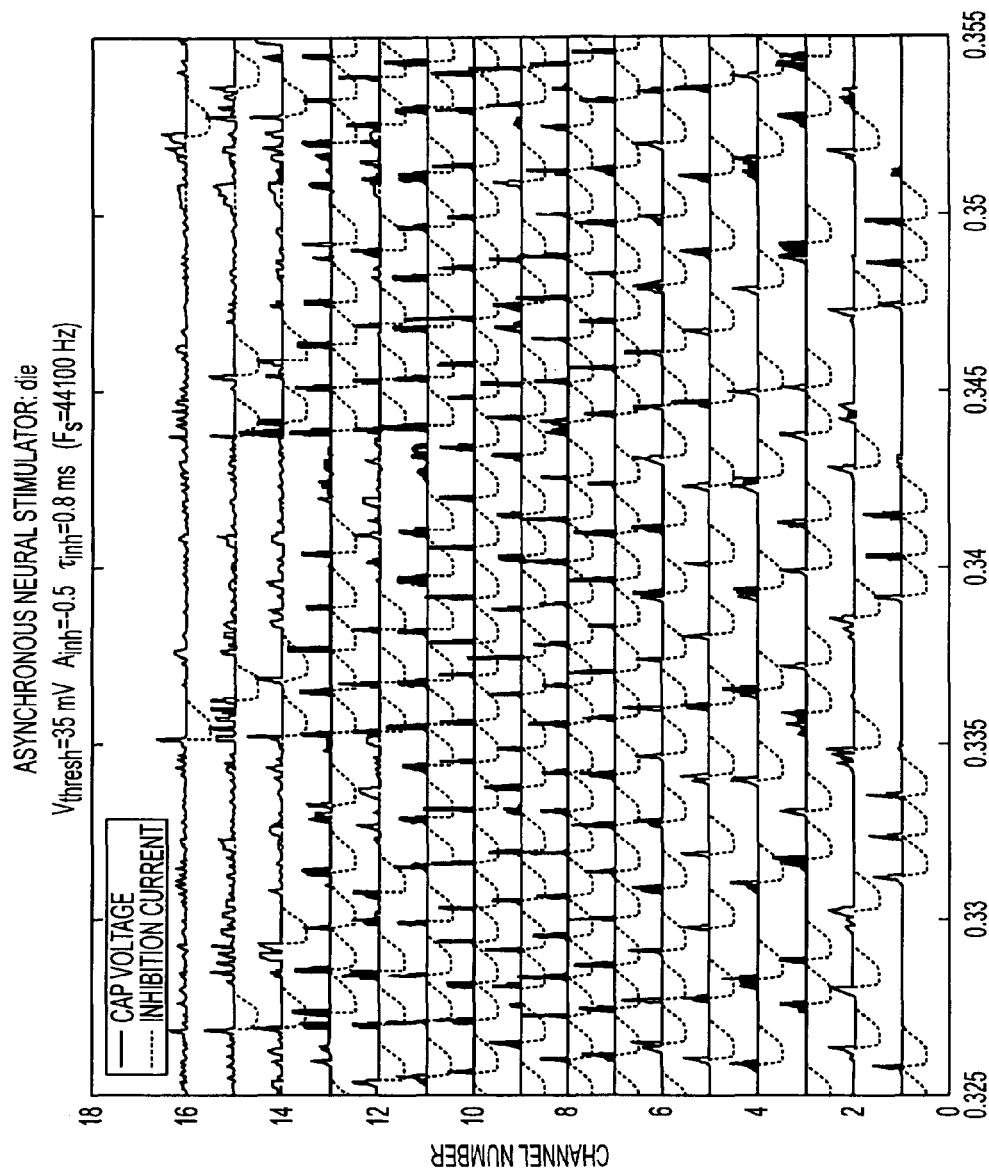
FIGS. 4A-4E are graphs showing illustrative results of the simulation of FIGS. 3A-B.
Figure 4B:
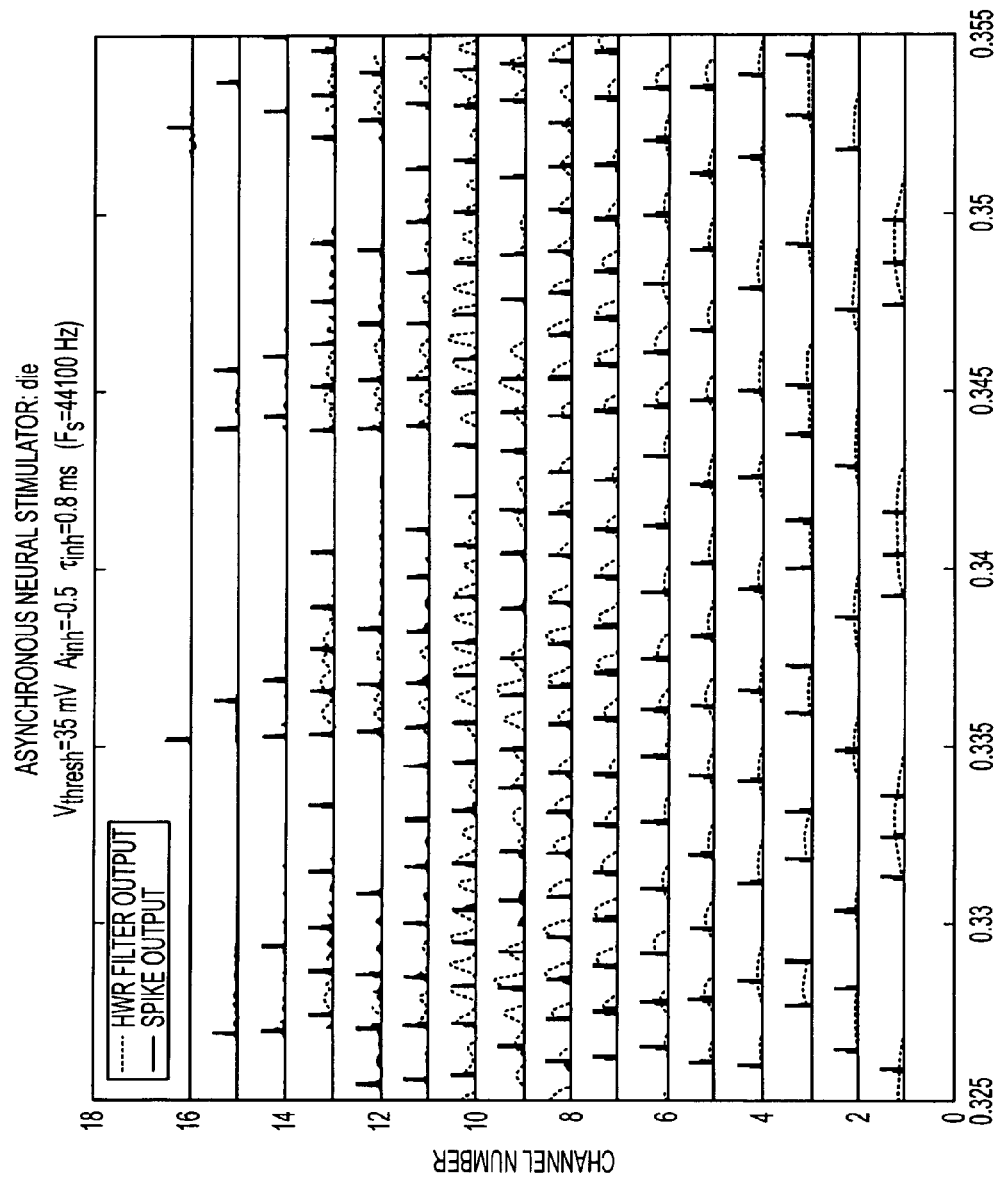
Figure 4C:
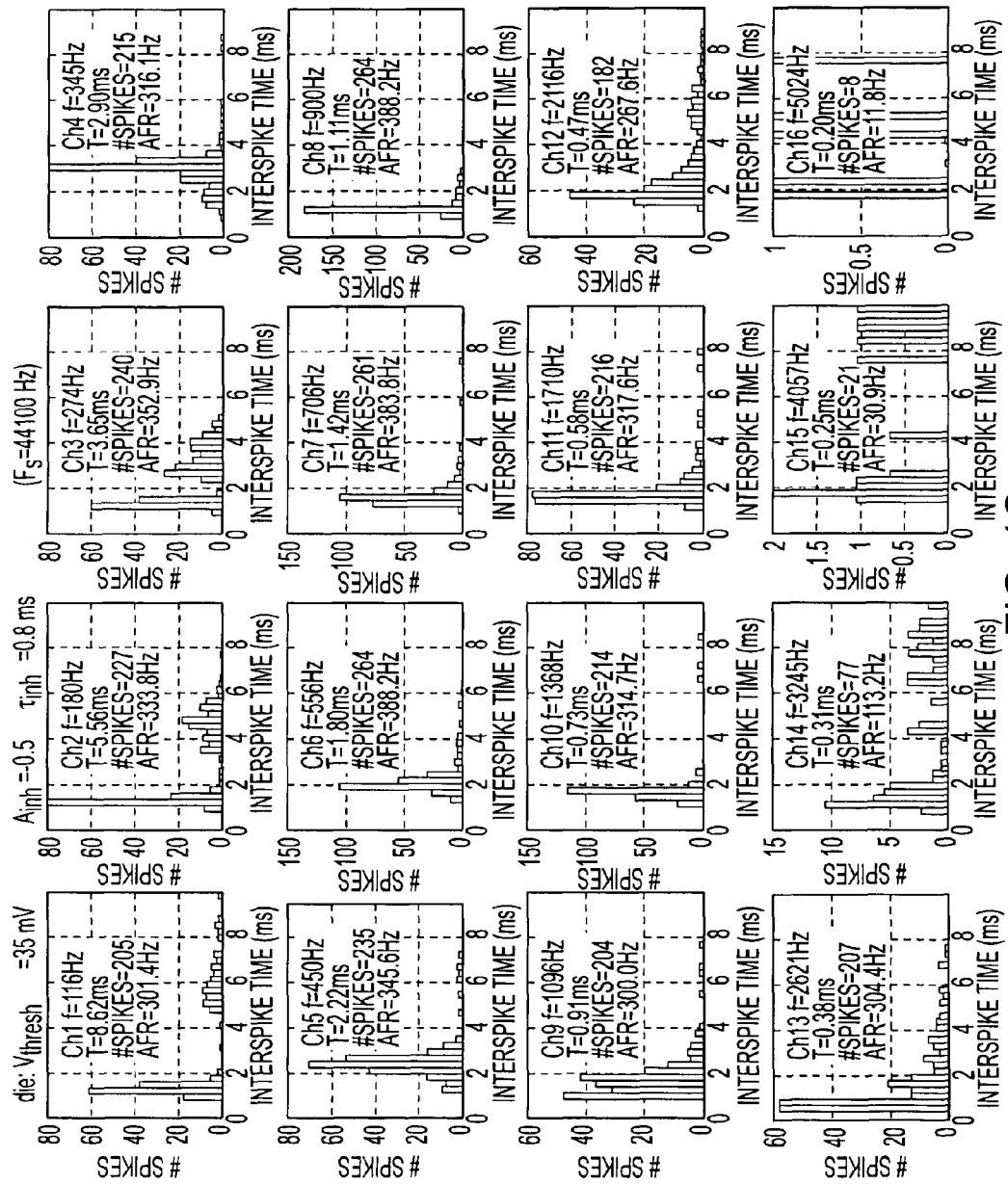

FIGS. 4A-4C provide graphs showing illustrative results of a simulation of a sound file of the word "die." In the simulation, each channel was modeled with a capacitor that is charged by the associated effective input signal, as described above. FIG. 4A illustrates (1) the voltage across the capacitor of each channel as a solid line, and (2) the inhibition current generated by each channel as a dotted line. FIG. 4B illustrates (1) half-wave rectified band-pass filter outputs (dashed line) that are used as input signals $S_P.x$ to the channel selection unit, and (2) corresponding output signals (solid line) output by the channel selection unit.

Delivery of phase information is important for higher order perception, in addition to the delivery of amplitude (or envelope) information that occurs in classical cochlear implants. Importantly, while the strategy of the present invention induces stochastic stimulation patterns, the channels with larger input signals "win" and fire more frequently than those with smaller input signals (as can be seen in FIG. 4B). By generating spike (and thus stimulation) pulses at times correlated to the strength of the input signals, the strategy of the present invention delivers coherent phase information to the nerves. Although the spike signals tend to be output near the beginning of each positive excursion in the input signal, there is a non-deterministic correlation between the time at which stimulation signals spike and the phase of the corresponding input signal. This creates a spread in the interspike interval histogram that is more biologically realistic but still is concentrated at the peak energy times.

FIG. 4C provides interspike interval histograms for the 16 simulation channels, center frequency "f" for each channel, period "T" for each channel (where T=1/f), the number of spikes for each channel, and average firing rate "AFR" for each channel. Spike intervals beyond 9 ms are not shown in the histograms. As indicated in FIG. 4C, the average firing rate for many of the channels approximately is between 300-388 Hz, and when averaged over all 16 channels, the average firing rate is 279 Hz. This is substantially less than the firing rates of many currently used cochlear implants, which are in the kHz range, and thus represents substantial power savings. In a preferred embodiment, the firing rate of an electrode corresponding to any channel is less than 1 kHz.

In the MATLAB simulation, a reconstruction of the original filter outputs was also implemented. After the outputs from the race-to-spike algorithm are scaled by the filter outputs at step 54, the resulting representative stimulation signals are passed through low-pass filters with the same Q and cut-off frequencies as the channel filters from step 48. Spike-based reconstruction using low-pass filtering has been proven effective in several neurophysical studies.

Figure 4D:
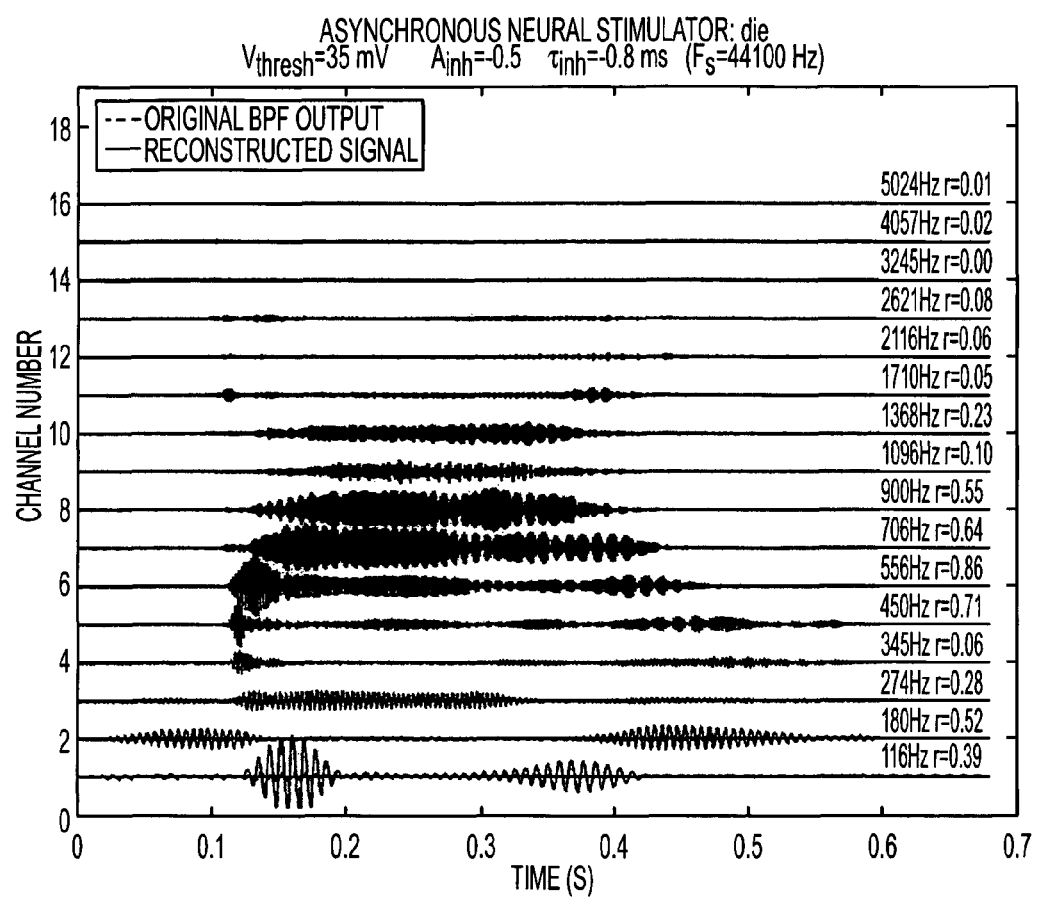
Figure 4E:
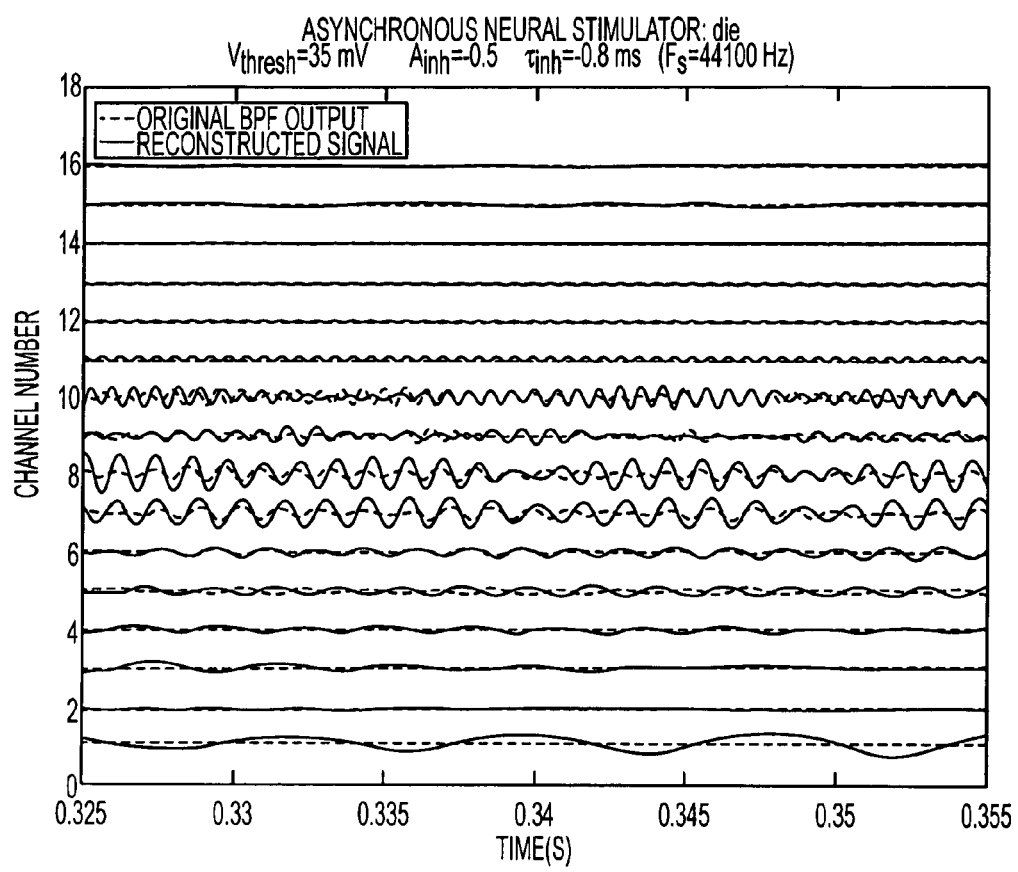

FIG. 4D shows a reconstruction of the original filter outputs of the 16 channels, while FIG. 4E is a magnified version of FIG. 4D. In particular, FIGS. 4D-E juxtaposes reconstructed signal (solid line) with the original band-pass filter output (dashed line) used as input signals $S_P.x$ to the simulation. Significantly, the reconstructed sounds retained an improved amount of tonal information in both language and music test sounds, and even on casual listening, the pitch and melody of the reconstructed sounds were unmistakable. It is notable that such quality and amounts of tonal information have rarely, if ever, been available to previous cochlear implant patients.

Figure 5A:
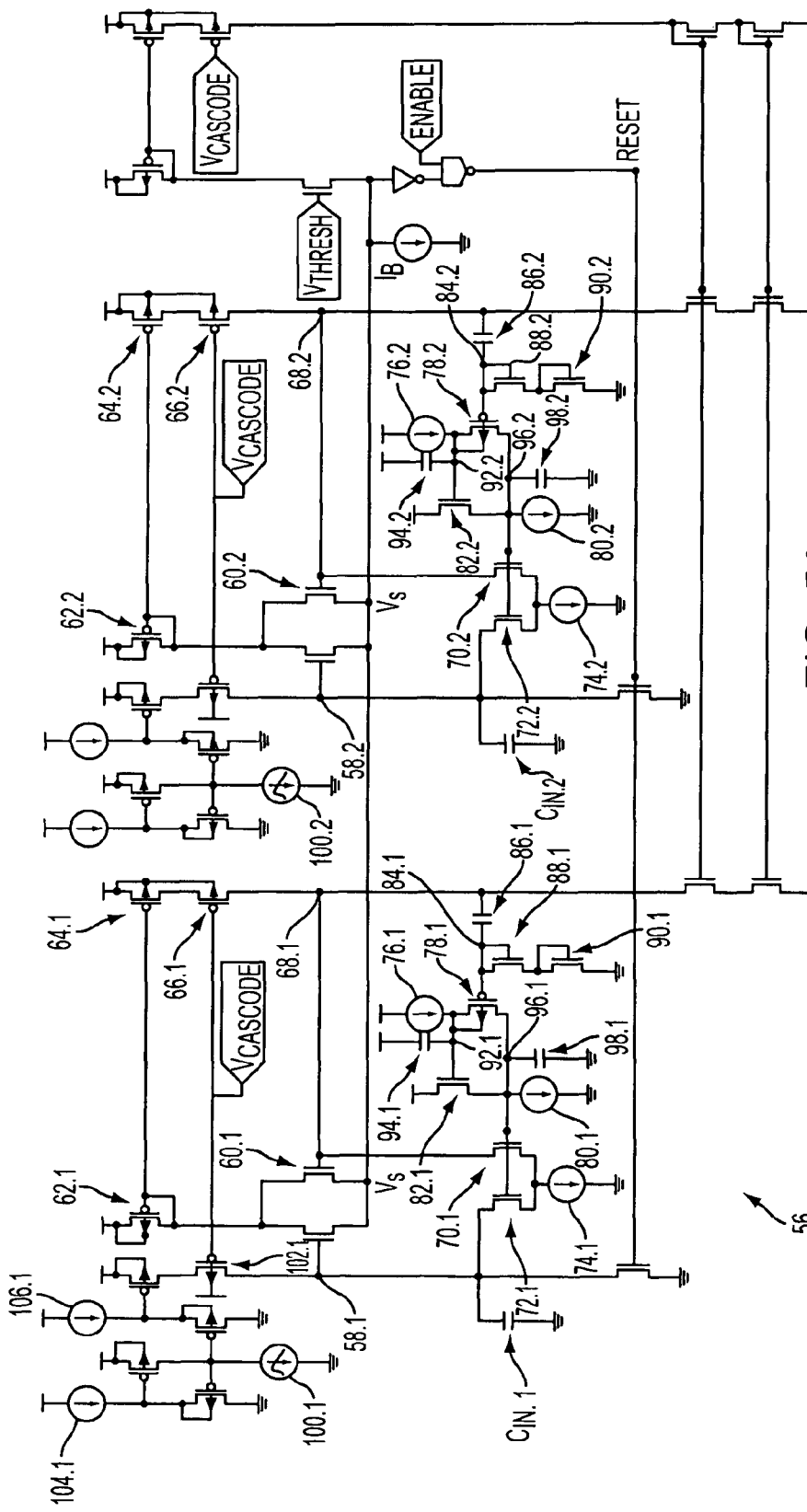
FIG. 5A is an illustrative circuit implementation of the channel selection strategy of the present invention.

Referring now to FIG. 5A, an analog circuit implementing the channel selection strategy of the present invention is presented. Circuit 56 comprises a two-channel selection unit that (1) determines the strongest of the two channels as a function of the time-varying input signals received from preprocessor 14, (2) generates a spike signal output for the winning channel for a predetermined amount of time $T_{WIN}$, and (3) generates an inhibition signal that weakens the input signal of the winning channel for a predetermined amount of time $T_{INH}$.

In operation, circuit 56 accepts input currents $I_{100.1}$ and $I_{100.2}$ of channels 1 and 2 (respectively) from preprocessor 14. The input currents are translated into input voltage magnitudes at nodes 58.1 and 58.2 (respectively). The first channel with an input voltage exceeding $V_{thresh}$ initiates a positive feedback loop around its corresponding transistors 60.x, 62.x, 64.x, and 66.x (where x denotes a channel number) that rapidly drives the output voltage at node 68.x of the winning channel to the rail. By being the first channel to rapidly pull up on voltage $V_S$, the winning channel suppresses all other channels from winning. Hence, no two channels can win simultaneously.

Whenever a positive feedback response is triggered, a reset circuit is employed to break the positive feedback clamp on all the nodes. Assuming for discussion purposes that channel 1 wins, output node 68.1 will shoot up to the rail voltage and be clamped there by positive feedback. An inhibition circuit then resets the positive feedback loop after a time $T_{WIN}$ (i.e., the amount of time during which the spike signal is generated) by pulling current out of output node 68.1 through transistor 70.1. The inhibition circuit then inhibits channel 1 from winning for a period of time approximately equal to $T_{INH}$ by drawing an inhibition current out of input node 58.1 through transistor 72.1. Because both transistors 70.1 and 72.1 are coupled to a single current source (i.e., sinking current source 74.1) in the present embodiment for convenience, the magnitudes of the reset current through transistor 70.1 and the inhibition current through transistor 72.1 are identical. In an alternative embodiment, the magnitudes of the reset current through transistor 70.1 and the inhibition current through transistor 72.1 need not be identical. Instead, each transistor may be coupled to independent current sources.

The inhibition circuit is derived from a super-buffer topology formed by current source 76.1, transistor 78.1, current source 80.1, and transistor 82.1. Assuming channel 1 wins, the voltage at output node 68.1 shoots up to the rail voltage. This rising edge is coupled into the voltage at node 84.1 through capacitor 86.1, and decays slowly with a time constant that is a function of the capacitance of capacitor 86.1 and the approximate two diode voltage drop across transistors 88.1 and 90.1. The rising edge also causes the voltage at node 92.1 to start pulling up. Since the voltage at node 92.1 is current limited by current source 76.1, the voltage rises with a slope equal to the ratio of the magnitude of current source 76.1 and the capacitance of capacitor 94.1. The voltage at node 96.1, however, is not current limited by transistor 82.1, which acts as an NMOS follower. This permits the voltage at node 96.1 to follow the voltage at node 92.1 until the voltage at node 96.1 reaches the voltage threshold for transistors 70.1 and 72.1 (which are equal in the embodiment of FIG. 5A).

The rate at which the voltage at node 96.1 increases and the voltage threshold of transistors 70.1 and 72.1 define the amount of time $T_{WIN}$ during which winning channel 1 generates a spike signal. In the embodiment of FIG. 5A, the "win" or spike time approximately equals $C_{94.1} * V_{TH,70.1}/I_{76.1}$, where $C_{94.1}$ is the capacitance of capacitor 94.1, $V_{TH,70.1}$ is the threshold voltage of transistor 70.1, and $I_{76.1}$ is the current magnitude of current source 76.1. As indicated by the preceding equation, the "win" or spike time may be programmed by adjusting the capacitance of capacitor 94.1, the threshold voltage of transistors 70.1 and 72.1 and/or the current strength of current source 76.1.

Once the voltage at node 96.1 exceeds that needed to draw a current equal to the magnitude of current source 74.1 through transistors 70.1 and 72.1, a current equal in magnitude to $I_{74.1}/2$ is pulled from each of nodes 58.1 and 68.1. To reset the positive feedback loop, current magnitude $I_{74.1}/2$ preferably is set high enough to overcome the magnitude of base current $I_B$.

Once transistor 70.1 is triggered, the voltage at output node 68.1 is pulled low. The falling edge of the voltage at the output node again is coupled to node 84.1 through capacitor 86.1. Transistor 78.1, now acting as a PMOS follower, pulls low, causing the voltage at node 92.1 to follow that at node 84.1. The voltage at node 96.1, which is current-limited by current source 80.1, discharges capacitor 98.1. As a result, the voltage at node 96.1 falls with a slope given by $(I_{80.1}-I_{76.1})/(C_{98.1}+C_{94.1})$, where $I_{80.1}$ is the current magnitude of current source 80.1, $I_{76.1}$ is the current magnitude of current source 76.1, $C_{98.1}$ is the capacitance of capacitor 98.1, and $C_{94.1}$ is the capacitance of capacitor 94.1. This slope reflects discharge of capacitors 98.1 and 94.1 by current source 80.1 at the same time as they are being charged by current source 76.1. Similar to the "win" or spike time $T_{WIN}$, inhibition time $T_{INH}$ is defined by $(C_{98.1}+C_{94.1})*V_{TH,70.1}/(I_{80.1}-I_{76.1})$, where $C_{98.1}$ is the capacitance of capacitor 98.1, $C_{94.1}$ is the capacitance of capacitor 94.1, $I_{80.1}$ is the magnitude of current source 80.1, and $I_{76.1}$ is the magnitude of current source 76.1. To inhibit the winning channel from winning approximately for the duration of inhibition period $T_{INH}$, current magnitude $I_{74.1}/2$ preferably also is set near the maximum magnitude transmitted by time-varying input current $I_{100.1}$.

Advantageously, the super-buffer topology presented in circuit 56 provides a right-half-plane zero for each channel due to the negative gain across transistor 78.x from the voltages at nodes 84.x to 96.x. The negative gain opposes the follower (or buffer) action that has a positive gain of 1. The right-half-plane zero induces an undershoot to the step response that reinforces spike period $T_{WIN}$ and inhibition period $T_{INH}$ with fixed and positive starting values.

It may be necessary to adjust the threshold of each individual channel, weight some channels more strongly than others, or equalize the relative strength/offsets of all channels. Rather than applying different thresholds, it is functionally equivalent to vary a gain factor on each input current. Also, since input capacitance $C_{IN}.x$ of each channel is fixed in fabrication, it may be desirable to scale all currents up or down to vary the overall integration time between winning spikes. To meet these two objectives, a gain stage, e.g., a translinear current gain mirror, may be added to the input of each channel. For example, for channel 1 in the embodiment of FIG. 5A, input current $I_{100.1}$ may be scaled by a gain factor dependent on current sources 104.1 and 106.1, resulting in an output current from transistor 102.1 approximately equal to $I_{104.1}/I_{106.1}*I_{100.1}$, where $I_{104.1}$ is the magnitude of current source 104.1 and $I_{106.1}$ is the magnitude of current source 106.1. Although the gain factor set by $I_{104.1}/I_{106.1}$ in the embodiment presented in FIG. 5A is identical for all channels, different gains may be applied to each channel by employing different current sources.

When any of the channels win, voltage $V_S$ goes high and triggers the "Reset" signal to go high. This grounds all the input capacitors $C_{IN}.x$ and resets circuit 56 to begin again after the spike time $T_{WTN}$ expires and voltage $V_S$ falls back to its nominal value. The "Enable" signal, if held low, holds the "Reset" signal high so that the channel selection algorithm is started only when the "Enable" signal goes high.

Because the circuit topology is symmetrical, circuit 56 behaves similarly for increases in the voltage at input node 58.2 of channel 2 relative to the voltage at input node 58.1 of channel 1. To extend the topology of circuit 56 to additional channels, additional circuit modules may be added to circuit 56.

Figure 5B:
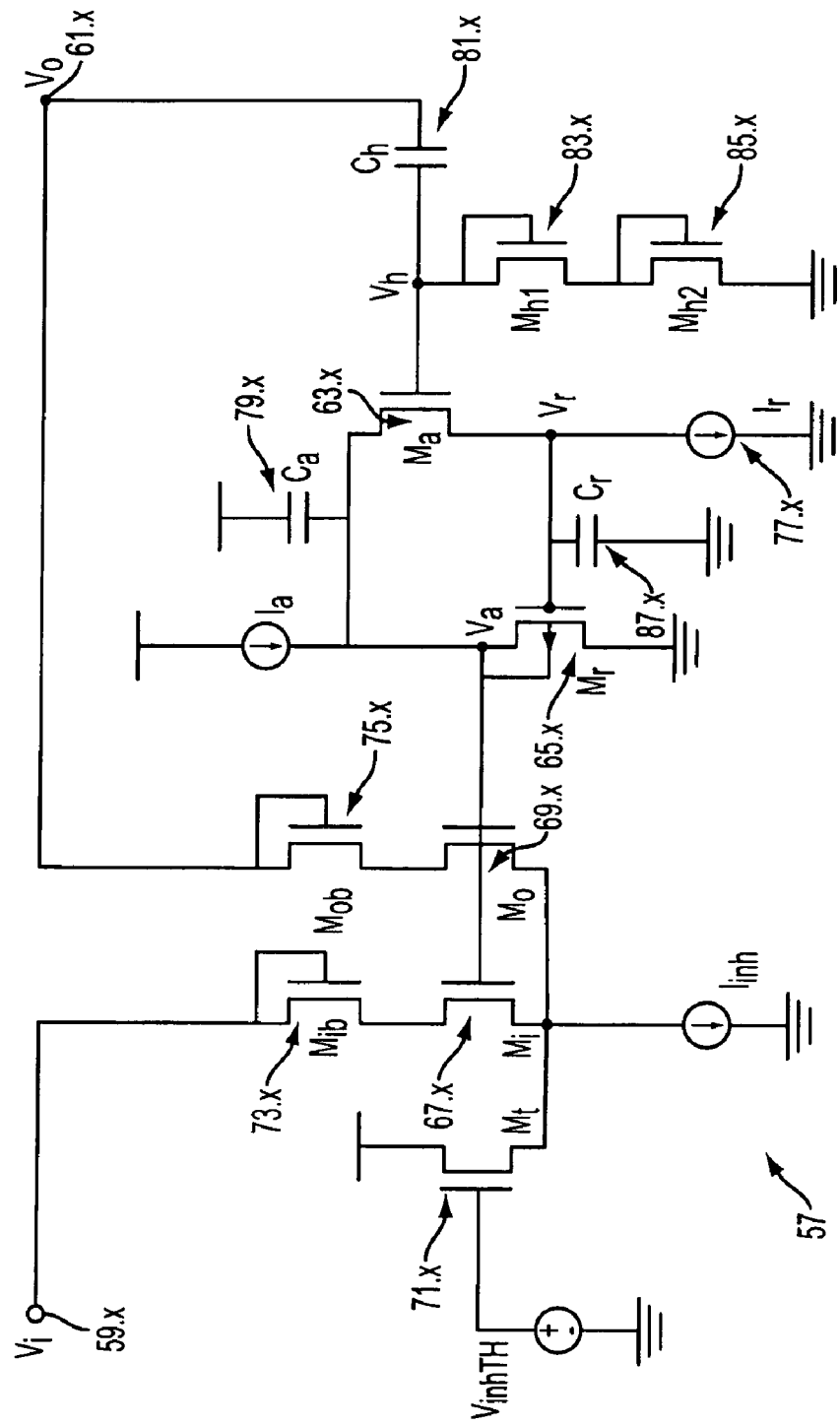
FIG. 5B is an alternative embodiment of the channel selection circuitry of FIG. 5A.

FIG. 5B presents an alternative embodiment of channel selection circuitry that performs more robustly under practical semiconductor fabrication constraints. The alternative embodiment comprises sub-circuit 57 of FIG. 5B and all components of circuit 56 of FIG. 5A except for components 70.x-98.x. That is, sub-circuit 57 replaces components 70.x-98.x of circuit 56 of FIG. 5A. Node 59.x of FIG. 5B is connected to node 58.x of FIG. 5A, and node 61.x of FIG. 5B is connected to node 68.x of FIG. 5A.

Sub-circuit 57 of FIG. 5B reverses the order of MOS devices 78.x and 82.x of circuit 56 so that the NMOS (transistor 63.x) is followed by the PMOS (transistor 65.x). This allows inhibition time $T_{INH}$ to be set solely by current $I_r$ of current source 77.x, rather than by the difference of two currents, $I_{80.1}$-$I_{76.1}$, as in circuit 56 of FIG. 5A. Thus, circuit 57 is more robust to fabrication variance.

Since voltage $V_r$ cannot sit quiescently below ground, the voltage at node 59.x that is driving transistors 67.x and 69.x sits quiescently around threshold voltage $V_{thp,65}$ of transistor 65.x. In contrast, the voltage at node 96.x in FIG. 5A sits around $V_{thp,78}$-$V_{thn,82}$, where (1) $V_{thp,78}$ is the threshold voltage for PMOS transistor 78.x, and (2) $V_{thn,82}$, which preferably has a value that is less than $V_{thp,78}$, is the threshold voltage for NMOS transistor 82.x. This causes the quiescent gate voltage provided to transistors 67.x and 69.x to sit above $V_{thn,63}$, which is the threshold voltage for NMOS transistor 63.x Circuit 57 also incorporates transistor 71.x, which thresholds transistors 67.x and 69.x. Transistor 71.x thresholds the output of transistors 67.x and 69.x such that transistors 67.x and 69.x will not output current unless voltage $V_a$ goes above voltage $V_{inhTH}$. Two diode-connected transistors 73.x and 75.x, which replace transistors 70.x and 72.x of FIG. 5A, are coupled to transistors 67.x and 69.x to block the flow of reverse current up through transistors 67.x and 69.x.

The choice of parameter values for capacitors 79.x, 81.x, and 87.x and transistors 83.x and 85.x are important. Capacitance $C_a$ of capacitor 79.x preferably is chosen to be parasitic in nature because the size of the right-half-plane zero undershoot is inversely proportional to capacitance $C_a$ and this will increase the undershoot. To further increase the undershoot, the capacitance $C_h$ of capacitor 81.x preferably is chosen to be as large as possible while taking into account area (e.g. 0.75 pF), and the width/length ratios for transistors 83.x and 85.x preferably are chosen to be as small as can be fabricated (e.g. minimum-sized devices). Also, capacitance $C_r$ of capacitor 87.x is chosen with the desired times of both $T_{WTN}$ and $T_{INH}$ in mind since (1) the length of $T_{WTN}$ in sub-circuit 57 is proportional to the sum of the capacitances of capacitors 79.x and 87.x, and (2) the length of $T_{INH}$ in sub-circuit 57 is proportional to capacitance $C_r$ of capacitor 87.x.

Figure 6A:
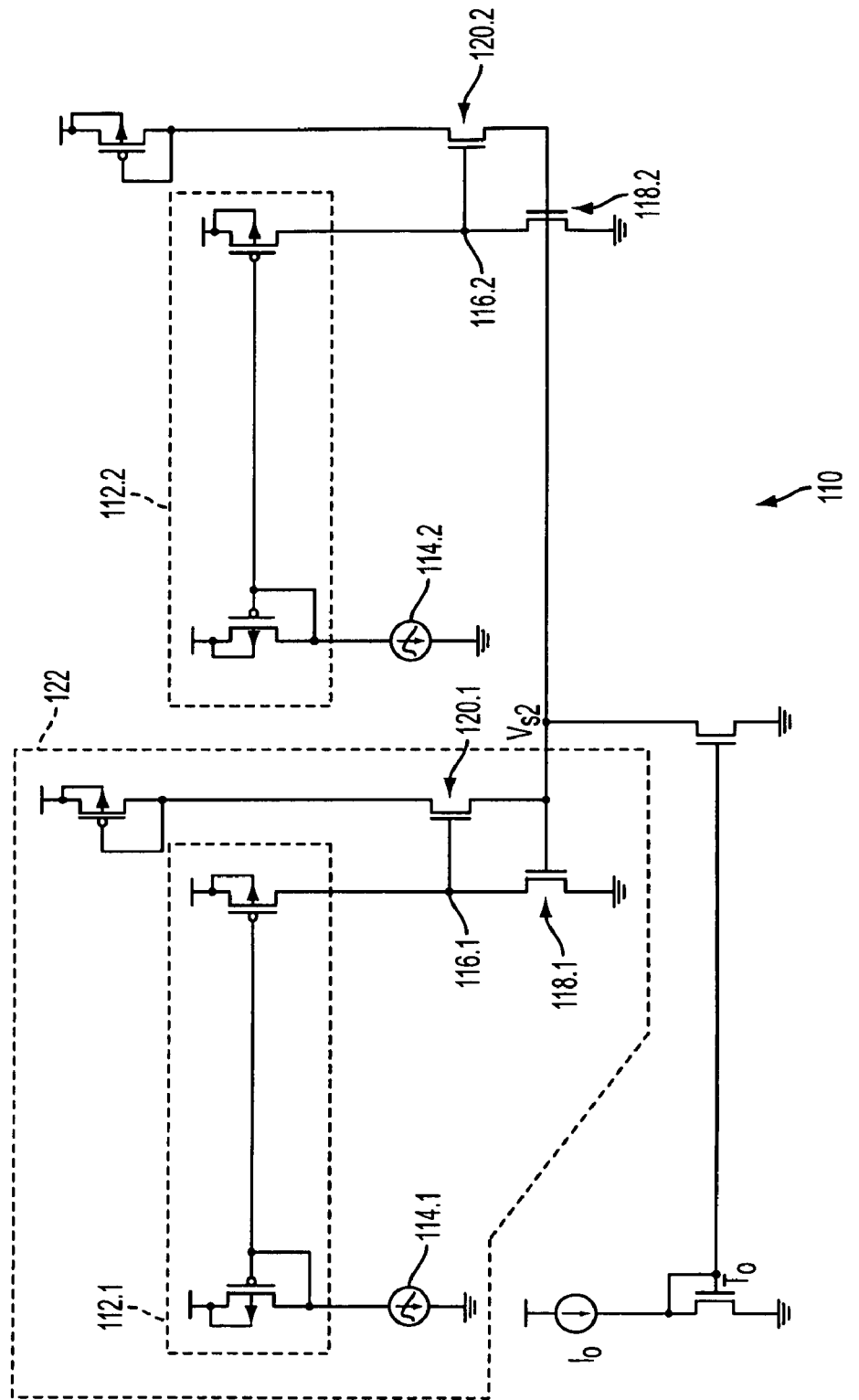
FIGS. 6A-6B are further alternative illustrative circuit implementations of the channel selection strategy of the present invention.
Figure 6B:
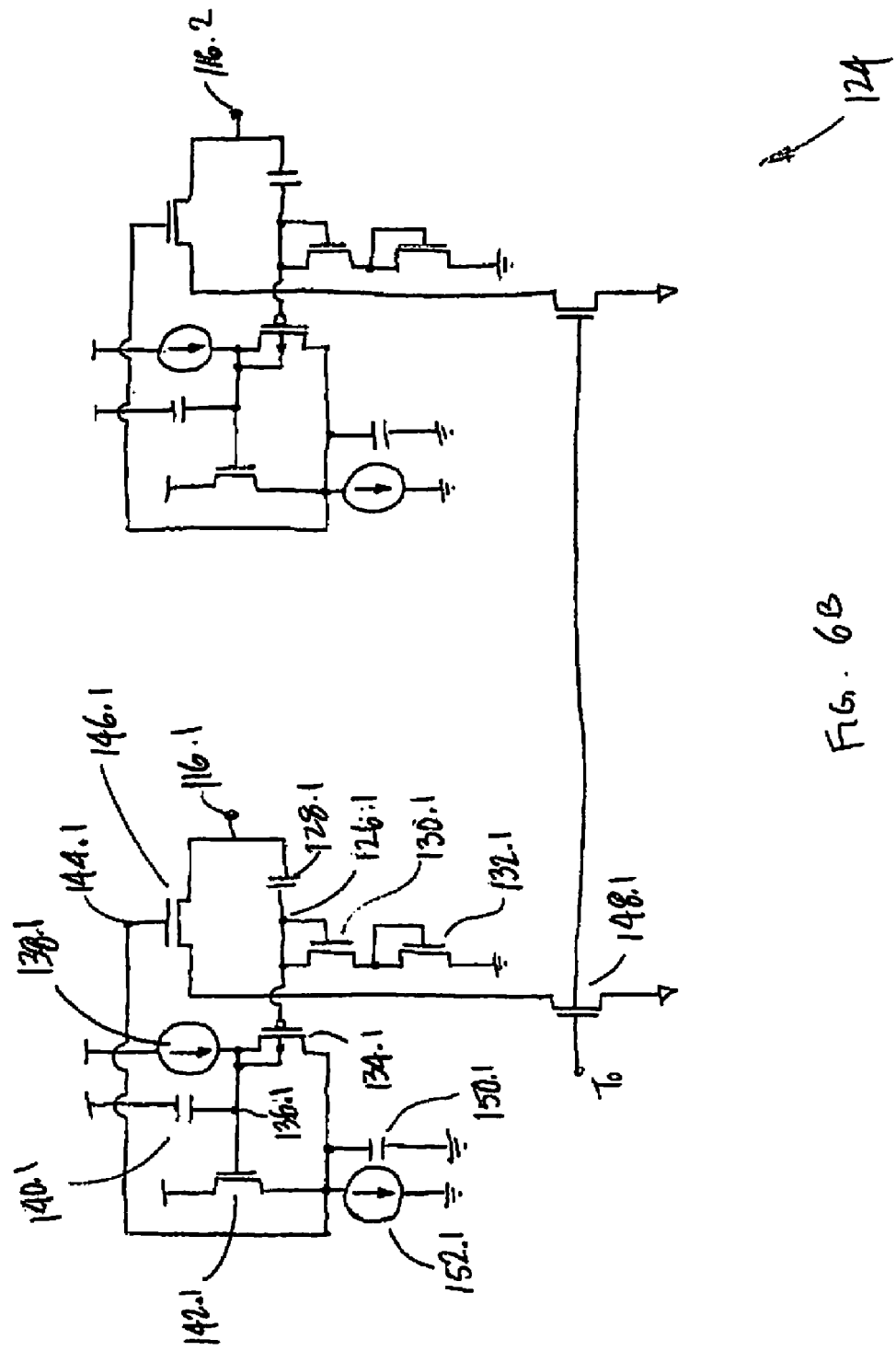

Referring now to FIGS. 6A-6B, a second embodiment of a channel selection unit of the present invention is presented. When superimposed, FIGS. 6A-6B illustrate two-channel selection unit 110 that (1) determines the strongest of the two channels from time-varying input signals received from preprocessor 14, (2) generates a spike signal for the electrode corresponding to the winning channel for a predetermined amount of time $T_{WTN}$, and (3) generates an inhibition signal that weakens the input signal of the winning channel for a predetermined amount of time $T_{INH}$. In contrast to the embodiment described with respect to FIGS. 5A-B, selection unit 110 of FIGS. 6A-6B immediately determines the strongest channel from the input signals, as opposed to waiting for the strongest input signal to reach threshold voltage $V_{thresh}$. This is equivalent to setting threshold voltage $V_{thresh}$ in FIGS. 5A-B to be zero. Selection unit 110 then suppresses the non-winning channel until the effective input signal magnitude of the non-winning channel exceeds the effective input signal magnitude of the winning channel (i.e., the input signal magnitude of the winning channel minus the generated inhibition signal magnitude). The following describes the behavior of the two-channel selection circuit if the input current of channel 1 is greater than the input current of channel 2.

In operation, circuit 110 accepts time-varying input currents $I_{114.1}$ and $I_{114.2}$ of channels 1 and 2 (respectively) from preprocessor 14. Current mirror 112.1 mirrors input current $I_{114.1}$ so that a current of equal or proportional strength flows through node 116.1. Likewise, current mirror 112.2 mirrors input current $I_{114.2}$ so that a current of equal or proportional strength flows through node 116.2. When the current flowing through node 116.1 increases relative to that flowing through node 116.2, transistor 118.1 must sink more current, causing the gate voltage of transistor 118.1 to rise. Because transistors 118.1 and 118.2 of channels 1 and 2 share a common gate, and thus have common gate voltage $V_{S2}$, transistor 118.2 also attempts to sink the same amount of current as that flowing through node 116.1. However, because the current flowing through node 116.2 is less than that flowing through node 116.1, the voltage at node 116.2 decreases to compensate. For large differences between the currents flowing through nodes 116.1 and 116.2, the voltage at node 116.2 reduces to zero volts, while the voltage at node 116.1 becomes a logarithmic function of input current $I_{114.1}$. Because the voltage at node 116.2 (and thus the gate voltage of transistor 120.2) is zero, no current flows through transistor 120.2. In contrast, tail current $I_O$ or a current proportional thereto flows through transistor 120.1. This current then may be mirrored out by a current mirror (not shown) as the spike signal for channel 1. Alternatively, this current may be mirrored out by a current mirror (not shown) and further processed before being employed as the spike signal.

Because the circuit topology is symmetrical, circuit 110 behaves similarly for increases in the current flowing through node 116.2 relative to the current flowing through node 116.1. To extend the topology of circuit 110 to additional channels, additional circuit modules 122 may be added to circuit 110.

FIG. 6B illustrates two-channel inhibition circuit 124 comprising an inhibition circuit module for each of circuit modules 122 of FIG. 6A. The following describes the behavior of inhibition circuit 124 if channel 1 "wins" as a result of having a stronger input signal than channel 2.

In operation, after channel 1 "wins," the voltage at node 116.1 increases to a level that is a logarithmic function of input current $I_{114.1}$. This rising edge is coupled into the voltage at node 126.1 through capacitor 128.1 and decays slowly with a time constant that is a function of the capacitance of capacitor 128.1 and the approximate two diode voltage drop across transistors 130.1 and 132.1. Transistor 134.1, acting as a PMOS follower, causes the voltage at node 136.1 to increase along with the voltage at node 116.1. The rate at which the voltage at node 136.1 increases is equal to the ratio of current $I_{138.1}$ of current source 138.1 to the capacitance of capacitor 140.1 (i.e., at a rate of $I_{138.1}/C_{140.1}$). Transistor 142.1, which acts as an NMOS follower, causes the voltage at node 144.1 to follow the voltage at node 136.1 until the voltage at node 144.1 reaches the voltage threshold of transistor 146.1 (i.e., $V_{TH,146.1}$). The rate at which the voltage at node 144.1 increases and the voltage threshold of transistor 146.1 defines the amount of time $T_{WIN}$ during which winning channel 1 generates a spike signal. In particular, the winning time approximately equals $C_{140.1}*V_{TH,146.1}/I_{138.1}$. As indicated by the preceding equation, the winning time may be programmed by adjusting the capacitance of capacitor 140.1, the threshold voltage of transistor 146.1 and/or the current strength of current source 138.1.

Once the voltage at node 144.1 reaches the threshold voltage of transistor 146.1, transistor 146.1 turns on and sinks some or all of the current mirrored from input current $I_{114.1}$. In particular, transistors 146.1 and 148.1 sink an initial inhibition current equal or proportional to tail current $I_O$ (or a current proportional thereto) from current mirrored from input current $I_{114.1}$. This reduces the strength of current flowing through node 116.1 of channel 1, thereby inhibiting channel 1 from winning until the inhibition current decreases to an appropriate level.

Thereafter, the voltage at node 116.1 decreases to zero volts. The decreasing voltage at node 116.1 is coupled to the voltage at node 126.1 through capacitor 128.1. Transistor 134.1 causes the voltage at node 136.1 to decrease along with the voltage at node 126.1. Transistor 142.1 in turn causes the voltage at node 144.1 to decrease along with the voltage at node 136.1. The rate at which the voltage at node 144.1 decreases is current limited, however, by the rate at which capacitor 150.1 is discharged. Capacitor 150.1 is discharged by current source 152.1 at the same time it is being charged by current source 138.1. Accordingly, the voltage at node 144.1 decreases at a rate equal to $(I_{152.1}-I_{138.1})/C_{150.1}$, where $C_{150.1}$ is the capacitance of capacitor 150.1. The decrease in the voltage at node 144.1 causes the inhibition current set by transistor 148.1 also to decrease in an exponential fashion. The rate at which the voltage at node 144.1 decreases and the voltage threshold of transistor 146.1 defines the amount of time $T_{INH}$ during which winning channel 1 generates an inhibition signal. In particular, the inhibition time approximately equals $C_{150.1}*V_{TH,146.1}/(I_{152.1}-I_{138.1})$. As indicated by the preceding equation, the inhibition time may be programmed by adjusting the capacitance of capacitor 150.1, the threshold voltage of transistor 146.1, the current strength of current source 138.1 and/or the current strength of current source 152.1. Once the inhibition is turned off—that is, once the voltage at node 144.1 has decreased to a certain level—channel 1 concludes a single channel selection period and can compete with channel 2 once again. As used herein, the term "a channel selection period" for a particular channel is defined as the aggregate of the winning and inhibition times of that channel.

Advantageously, the super-buffer topology illustrated in circuit 124 provides a right-half-plane zero due to the negative gain between nodes 126.1 and 144.1 across transistor 134.1. That negative gain opposes the buffering action of transistor 134.1, which has a positive gain of one. The right-half-plane zero reinforces the winning and inhibition times with fixed and positive starting values.

Figure 7A:
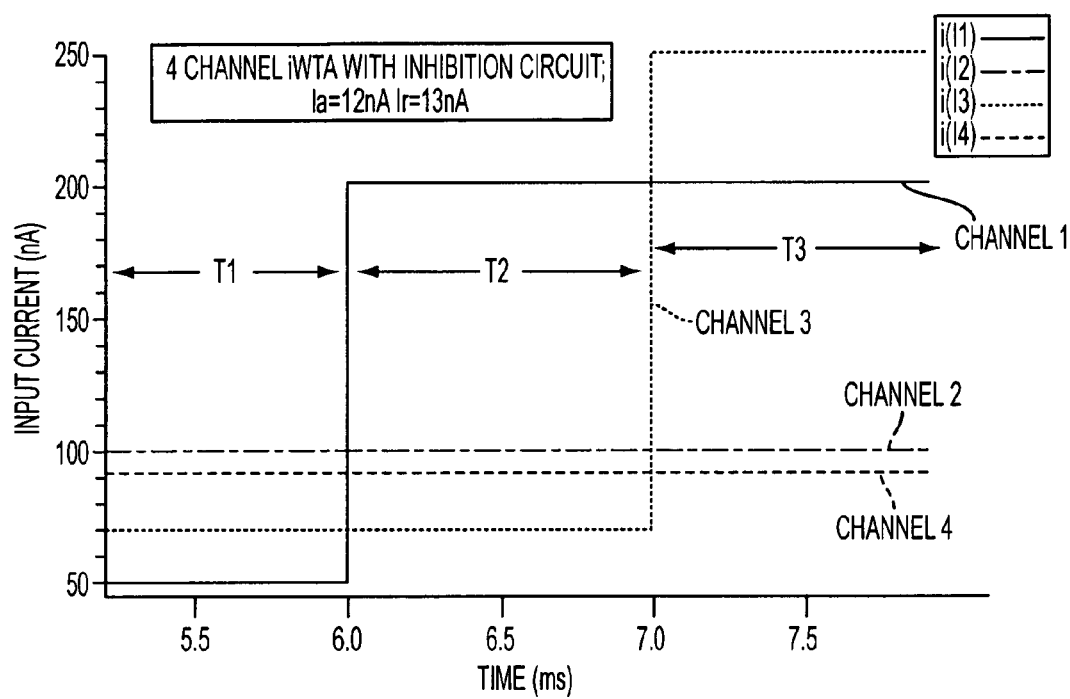
FIGS. 7A-7C are graphs showing illustrative results of a simulation of the circuit implementation of FIGS. 6A-6B.
Figure 7B:
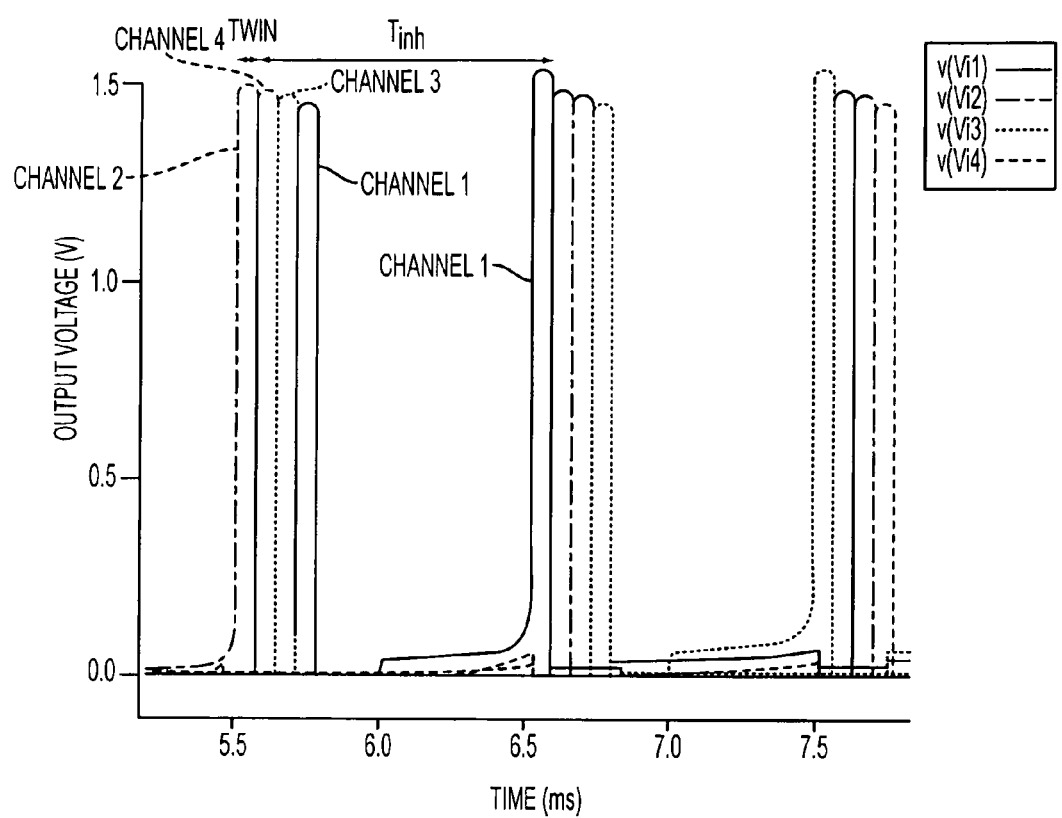
Figure 7C:
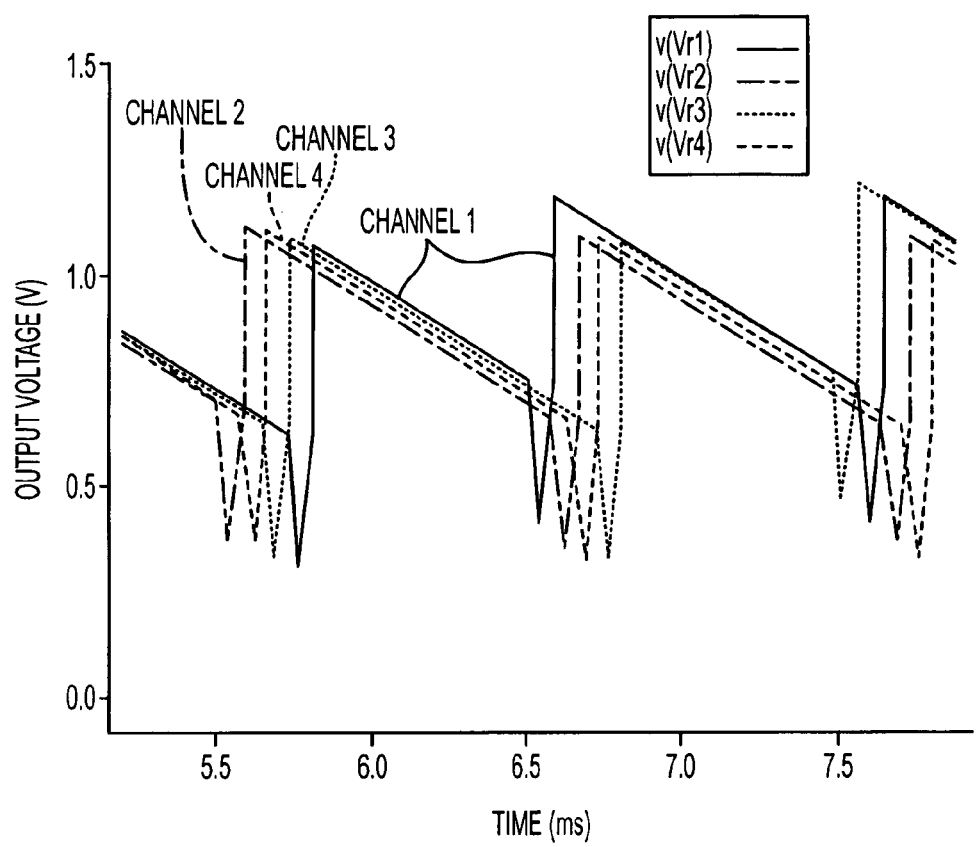

While the embodiments of FIGS. 5A-B and 6A-6B are illustrated with only two channels, it should be apparent to one of ordinary skill in the art that additional channels may be added. Indeed, applicants simulated a 4-channel selection unit similar to the unit illustratively provided in FIGS. 6A-6B. FIG. 7A illustrates the input currents for all four channels of the simulated 4-channel selection unit. FIG. 7B illustrates the voltage response at node 116.x of each channel x. FIG. 7C illustrates the voltage response at node 144.x of each channel x. As depicted in the graphs, channel 2, experiencing the strongest input current at time period T1, wins during time period T1. Once an inhibition signal is generated for channel 2, channel 2 is inhibited from winning again during time period T1, thereby permitting the next strongest channel (i.e., channel 4) to win. Thus, the strongest channel at each winning time fires first, and then gives way to the next strongest channel. In this manner, channel selection is asynchronously determined.

For the circuit used to generate the graphs of FIGS. 7A-7C, all four channels were programmed with the same winning times and the same inhibition times. Furthermore, the inhibition time was programmed to be more than four times the winning time. This permits all four channels of the circuit to be selected within one channel selection period, albeit in an asynchronous, stochastic manner. However, if the inhibition time is programmed to be less than four times the winning time, fewer than all four channels may be selected asynchronously to generate spike signals within one channel selection period. Advantageously, this permits weaker channels (that is, channels having less energy than other channels) to remain present in neural stimulation without requiring the same rate of stimulation as stronger channels, potentially saving power.

The architecture of the circuits presented in FIGS. 5A-B and 6A-6B particularly are suited for low-power or ultra-low-power analog circuit implementations to achieve high timing resolution without fast digital clock circuits. In particular, unlike a fixed-rate stimulation strategy in which information is transmitted at a fixed rate regardless of whether such information is needed or not, the strategy of the present invention increases bandwidth.

While the circuit used to generate the graphs of FIGS. 7A-7C was programmed so that all channels were programmed with the same winning times and the same inhibition times, one of ordinary skill in the art will recognize that the winning and inhibition times of each channel may be programmed independently of the other channels in the system.

Although particular embodiments of the present invention have been described above in detail, it will be understood that this description is merely for purposes of illustration. For example, any of the parameters discussed above that may be arbitrarily complex functions may be determined empirically so as to achieve a performance that is most appropriate to the application or user. Also, while the above-described embodiments inhibit more than one channel from being stimulated at any given time by inhibiting more than one channel from winning, it should be apparent to one of ordinary skill in the art that more than one channel may be configured to "win." For example, two or more channels may be configured to win at any given time so that the associated electrodes are stimulated during overlapping stimulation time periods. In one embodiment, only two channels are configured to win at any given time so that only two electrodes fire at any given time. In the latter embodiment, the remaining electrodes are inhibited from being stimulated simultaneously with the electrodes corresponding to the two winning channels. Furthermore, while the above-described embodiments output a spike signal to indicate the winning channel or channels, any type of output signal may be provided. Also, while the embodiments described above correlate a single electrode to a single channel, it should be understood that multiple electrodes may correspond to a single channel, multiple channels may correspond to a single electrode, or multiple channels may correspond to multiple electrodes. Specific features of the invention are shown in some drawings and not in others, for purposes of convenience only, and any feature may be combined with other features in accordance with the invention. Steps of the described strategies may be reordered or combined, and other steps may be included. Further variations will be apparent to one skilled in the art in light of this disclosure and such variations are intended to fall within the scope of the appended claims.

What is claimed is:

1. A method for stimulating a plurality of electrodes in a neural implant, wherein each one of the plurality of electrodes is associated with one of a plurality of channels, the method comprising:
   accepting an input signal in each of the channels, each of the input signals representative of a sensory environment;
   adjusting one or more of the input signals by one or more corresponding inhibition signals to generate an effective input signal for each of the channels, each of the effective input signals having an effective input magnitude;
   selecting a channel from among the plurality of channels as a winning channel based on the effective input magnitudes of the effective input signals, the winning channel having an effective input signal with the largest effective input magnitude out of all of the effective input signals;
   generating an output signal for the selected channel; and
   selectively generating an inhibition signal for the selected channel in accordance with an inhibition scheme, the inhibition signal having an initial maximum magnitude that decays over a predetermined period of time;
   wherein the inhibition signal is configured to reduce a strength of an input signal corresponding to the selected channel in order to reduce a likelihood that the selected channel will be subsequently selected as the winning channel during the predetermined period of time.

2. The method of claim 1, wherein the generating of the output signal comprises generating the output signal for an output time period that is predetermined.

3. The method of claim 1, further comprising:
   selecting another channel from among the plurality of channels as the winning channel based on the effective input magnitudes of the effective input signals;
   generating another output signal for the other selected channel; and
   selectively generating another inhibition signal for the other selected channel in accordance with the inhibition scheme.

4. The method of claim 3, further comprising:
   generating a stimulation signal for stimulating an electrode corresponding to the selected channel for a first stimulation time period; and
   generating a stimulation signal for stimulating an electrode corresponding to the other selected channel for a second stimulation time period,
   wherein the first and second stimulation time periods overlap.

5. The method of claim 3, further comprising:
   generating a stimulation signal for stimulating an electrode corresponding to the selected channel for a first stimulation time period; and
   generating a stimulation signal for stimulating an electrode corresponding to the other selected channel for a second stimulation time period,
   wherein the first and second stimulation time periods do not overlap.

6. The method of claim 3, further comprising permitting the other inhibition signal to decay over time.

7. The method of claim 3, further comprising:
   generating stimulation signals for stimulating electrodes corresponding to the selected channel and the other selected channel; and
   inhibiting more than two electrodes from being stimulated at any given time.

8. The method of claim 3, further comprising generating stimulation signals for stimulating electrodes corresponding to the selected channel and the other selected channel, wherein each electrode corresponding to the selected channel and the other selected channel is stimulated at a rate less than 1 kHz.

9. The method of claim 1, further comprising:
   generating a stimulation signal for stimulating an electrode corresponding to the selected channel; and
   inhibiting more than one electrode from being stimulated at any given time.

10. The method of claim 1, wherein the inhibition signal has a magnitude that inhibits the effective input signal corresponding to the selected channel from having the largest effective input magnitude for an inhibition time period.

11. The method of claim 1, further comprising integrating the effective input signal of each channel,
    wherein:
    each channel has a corresponding threshold, and
    wherein the selecting of the channel as the winning channel comprises selecting a channel within the plurality of channels having a corresponding effective input signal that integrates up to its corresponding threshold before the effective input signals of any of the other channels within the plurality of channels integrate up to their corresponding thresholds.

12. The method of claim 11, wherein the thresholds of two or more of the plurality of channels are the same.

13. The method of claim 11, wherein the thresholds of two or more of the plurality of channels are different.

14. The method of claim 11, wherein the threshold of at least one of the plurality of channels is constant over time.

15. The method of claim 11, wherein the threshold of at least one of the plurality of channels varies over time.

16. The method of claim 1, wherein the selecting of the channel as the winning channel comprises selecting a channel within the plurality of channels so that phase information correlated with the input signals is incorporated.

17. The method of claim 1, wherein the selectively generating the inhibition signal comprises selectively generating a inhibition signal having a magnitude dependent on the input signals.

18. The method of claim 1, further comprising scaling one or more of the input signals by a gain factor.

19. The method of claim 18, wherein the scaling of one or more of the input signals comprises using a gain stage to scale the one or more of the input signals.

20. The method of claim 1, further comprising generating and outputting a baseline signal for all of the channels except the selected channel, the baseline signal having a baseline magnitude and the first output signal having an output magnitude, wherein the baseline magnitude is different from the output magnitude.

21. The method of claim 1, wherein the neural implant comprises a cochlear implant and the input signals are representative of a sound environment.

22. The method of claim 1, further comprising combining the input signal of the selected channel with the output signal to produce a stimulation signal.

23. The method of claim 22, further comprising stimulating an electrode corresponding to the selected channel with a signal that is a function of the stimulation signal.

24. A neural implant system comprising:
a plurality of electrodes; and
a signal processing unit coupled to the plurality of electrodes, each electrode of the plurality of electrodes having a corresponding channel in the signal processing unit, the signal processing unit having a channel selection unit configured to:
  accept an input signal in each of the channels, each of the input signals representative of a sensory environment;
  adjust one or more of the input signals by one or more corresponding inhibition signals to generate an effective input signal for each of the channels, each of the effective input signals having an effective input magnitude;
  select a channel from among the plurality of channels as a winning channel based on the effective input magnitudes of the effective input signals, the winning channel having an effective input signal with the largest effective input magnitude out of all of the effective input signals;
  generate an output signal for the selected channel; and
  selectively generate an inhibition signal for the selected channel in accordance with an inhibition scheme, the inhibition signal having an initial maximum magnitude that decays over a predetermined period of time;
  wherein the inhibition signal is configured to reduce a strength of an input signal corresponding to the selected channel in order to reduce a likelihood that the selected channel will be subsequently selected as the winning channel during the predetermined period of time.

25. The system of claim 24, wherein the channel selection unit is configured to generate the output signal for an output time period that is predetermined.

26. The system of claim 24, wherein the channel selection unit further is configured to:
  select another channel from among the plurality of channels as the winning channel based on the effective input magnitudes of the effective input signals;
  generate another output signal for the other selected channel, and
  selectively generate another inhibition signal for the other selected channel in accordance with the inhibition scheme.

27. The system of claim 26, wherein the neural implant system further is configured to:
  generate a first stimulation signal to stimulate the electrode corresponding to the selected channel for a first stimulation time period,
  generate a second stimulation signal to stimulate the electrode corresponding to the other selected channel for a second stimulation time period,
  wherein the first and second stimulation time periods overlap.

28. The system of claim 26, wherein the neural implant system further is configured to:
  generate a first stimulation signal to stimulate an electrode corresponding to the selected channel for a first stimulation time period,
  generate a second stimulation signal to stimulate an electrode corresponding to the other selected channel for a second stimulation time period,
  wherein the first and second stimulation time periods do not overlap.

29. The system of claim 26, wherein the channel selection unit further is configured to permit the other inhibition signal to decay over time.

30. The system of claim 26, wherein the neural implant system further is configured to:
  generate stimulation signals for stimulating electrodes corresponding to the selected channel and the other selected channel; and
  inhibit more than two electrodes from being stimulated at any given time.

31. The system of claim 26, wherein the neural implant system further is configured to:
  generate stimulation signals for stimulating electrodes corresponding to the selected channel and the other selected channel, wherein each electrode corresponding to the selected channel and the other selected channel is stimulated at a rate less than 1 kHz.

32. The system of claim 24, wherein the neural implant system further is configured to:
  generate a stimulation signal for stimulating an electrode corresponding to the selected channel; and
  inhibit more than one electrode from being stimulated at any given time.

33. The system of claim 24, wherein the inhibition signal has a magnitude that inhibits the effective input signal corresponding to the selected channel from having the largest effective input magnitude for an inhibition time period.

34. The system of claim 24, wherein:
  each channel within the plurality of channels has a corresponding threshold, and
  the channel selection unit further is configured to:
  integrate the effective input signal corresponding to each channel within the plurality of channels, and
  select the channel as the winning channel by selecting a channel within the plurality of channels having a corresponding effective input signal that integrates up to its corresponding threshold before the effective input signals of any of the other channels within the plurality of channels integrate up to their corresponding thresholds.

35. The system of claim 34, wherein the thresholds of two or more of the plurality of channels are the same.

36. The system of claim 34, wherein the thresholds of two or more of the plurality of channels are different.

37. The system of claim 34, wherein the threshold of at least one of the plurality of channels is constant over time.

38. The system of claim 34, wherein the threshold of at least one of the plurality of channels varies over time.

39. The system of claim 24, wherein the channel selection unit is configured to select the channel as the winning channel so that phase information correlated with the input signals is incorporated.

40. The system of claim 24, wherein the channel selection unit is configured to selectively generate the inhibition signal with a magnitude dependent on the input signals.

41. The system of claim 24, wherein the signal processing unit further is configured to scale one or more of the input signals by a gain factor.

42. The system of claim 41, wherein the signal processing unit comprises one or more gain stages to scale one or more of the input signals.

43. The system of claim 24, wherein the channel selection unit further is configured to generate and output a baseline signal for all of the channels except the selected channel, the baseline signal having a baseline magnitude and the first output signal having an output magnitude, wherein the baseline magnitude is different from the output magnitude.

44. The system of claim 24, wherein the neural implant comprises a cochlear implant and the input signals are representative of a sound environment.

45. The system of claim 44, wherein the signal processing unit further comprises a preprocessing unit having:
- a filter bank that separates signals representative of the sound environment into the channels; and
- an envelope detector for each of the channels, each envelope detector configured to accept output from the filter bank and estimate signal energy.

46. The system of claim 45, wherein the envelope detector for each of the channels comprises a half-wave or full-wave rectifier, each half-wave or full-wave rectifier configured to rectify output from the filter bank and provide input to the channel selection unit.

47. The system of claim 24, wherein the signal processing unit is configured to combine the input signal of the selected channel with the output signal to produce a stimulation signal.

48. A neural implant system comprising:
an electrode array comprising a plurality of electrodes; and
signal processing circuitry coupled to the electrode array, each electrode of the electrode array having a corresponding channel in the signal processing circuitry, the signal processing circuitry having channel selection circuitry configured to:
- accept an input signal in each of the channels, each of the input signals representative of a sensory environment;
- adjust one or more of the input signals by one or more corresponding inhibition signals to generate an effective input signal for each of the channels, each of the effective input signals having an effective input magnitude;
- select a channel from among the plurality of channels as a winning channel based on the effective input magnitudes of the effective input signals, the winning channel having an effective input signal with the largest effective input magnitude out of all of the effective input signals;
- generate an output signal for the selected channel; and
- selectively generate an inhibition signal for the selected channel, the inhibition signal having an initial maximum magnitude that decays over a predetermined period of time;
wherein the inhibition signal is configured to reduce a strength of an input signal corresponding to the selected channel in order to reduce a likelihood that the selected channel will be subsequently selected as the winning channel during the predetermined period of time.

* * * * *